United States Patent [19]

Hitchcock et al.

[11] Patent Number: 5,840,729
[45] Date of Patent: Nov. 24, 1998

[54] XANTHINE DERIVATIVES AS ADENOSINE A1 RECEPTOR ANTAGONISTS

[75] Inventors: Janice M. Hitchcock, Mundolsheim; Stephen M. Sorensen, Illkirch, both of France; Mark W. Dudley; Norton P. Peet, both of Cincinnati, Ohio

[73] Assignee: Merrell Pharmaceuticals Inc., Cincinnati, Ohio

[21] Appl. No.: 500,991
[22] PCT Filed: Jan. 27, 1994
[86] PCT No.: PCT/US94/01009
  § 371 Date: Dec. 18, 1995
  § 102(e) Date: Dec. 18, 1995
[87] PCT Pub. No.: WO94/19349
  PCT Pub. Date: Sep. 1, 1994

Related U.S. Application Data

[63] Continuation of Ser. No. 23,501, Feb. 26, 1993, abandoned.
[51] Int. Cl.[6] .......................... A61K 31/52; C07D 473/01
[52] U.S. Cl. .......................... 514/263; 514/262; 544/266; 544/267
[58] Field of Search ................................. 514/263, 262; 544/266, 267

[56] References Cited

U.S. PATENT DOCUMENTS 5,047,534  9/1991  Peet et al. ................ 514/263
5,281,607  1/1994  Stone et al. ............... 514/280

FOREIGN PATENT DOCUMENTS 0499175  2/1991  European Pat. Off. .
0374808  9/1992  European Pat. Off. .
0503563  9/1992  European Pat. Off. .
9200207  1/1992  WIPO .

OTHER PUBLICATIONS

Schingnitz, G., Selective $A_1$–Antagonists For Treatment Of Cognitive Deficits, *Nucleosides & Nucleotides*, 10(5), 1067–76 (1991).

Kalaria, *Biol. Abstr.*, 89(3):28690 (1989).

Arnsten et al., *Psychopharmacology*, vol. 108, pp. 159–169 (1992).

Shimada, Junichi et al., *J. Medicinal Chem.*, 1992, vol. 35, Mar. 1992, pp. 924–930.

Shimada, Junichi et al., *J. Medicinal Chem.*, 1991, vol. 34, Jan. 1991, pp. 466–469.

Peet, Norton et al., *J. Medicinal Chem.*, 1990, vol. 33, No. 12., pp. 3127–3130.

*Primary Examiner*—Theodore J. Criares
*Attorney, Agent, or Firm*—Michael J. Sayles

[57] ABSTRACT

A method of attenuating a cognitive deficit in a patient in need thereof comprising administering to the patient a xanthine derivative.

6 Claims, 5 Drawing Sheets

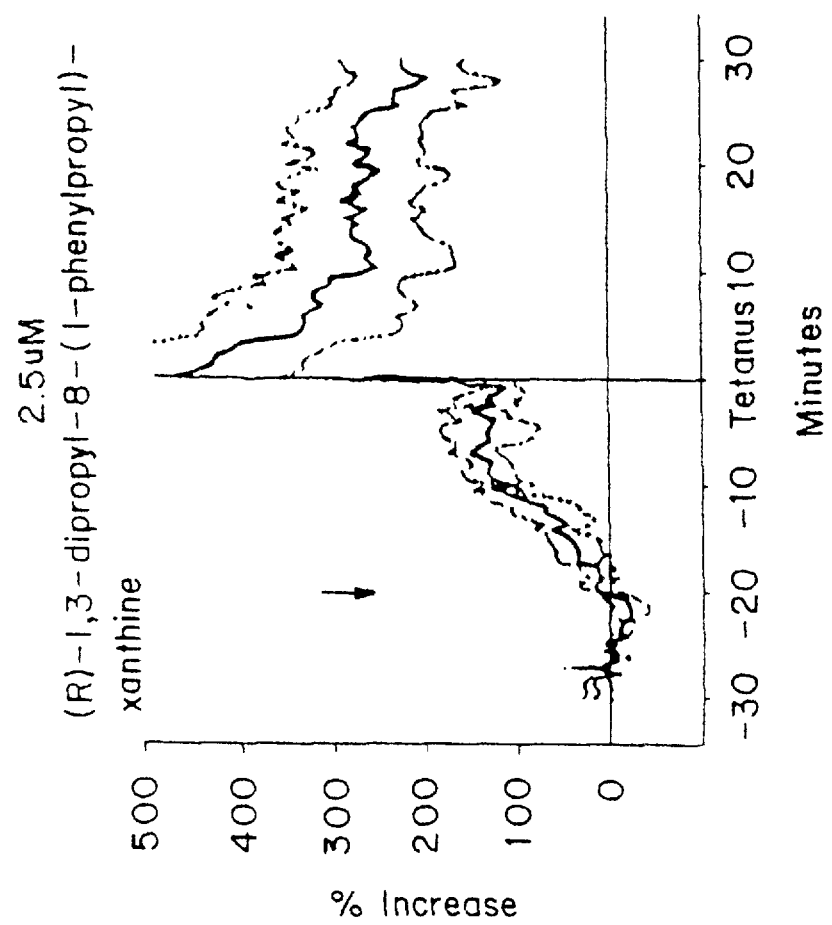

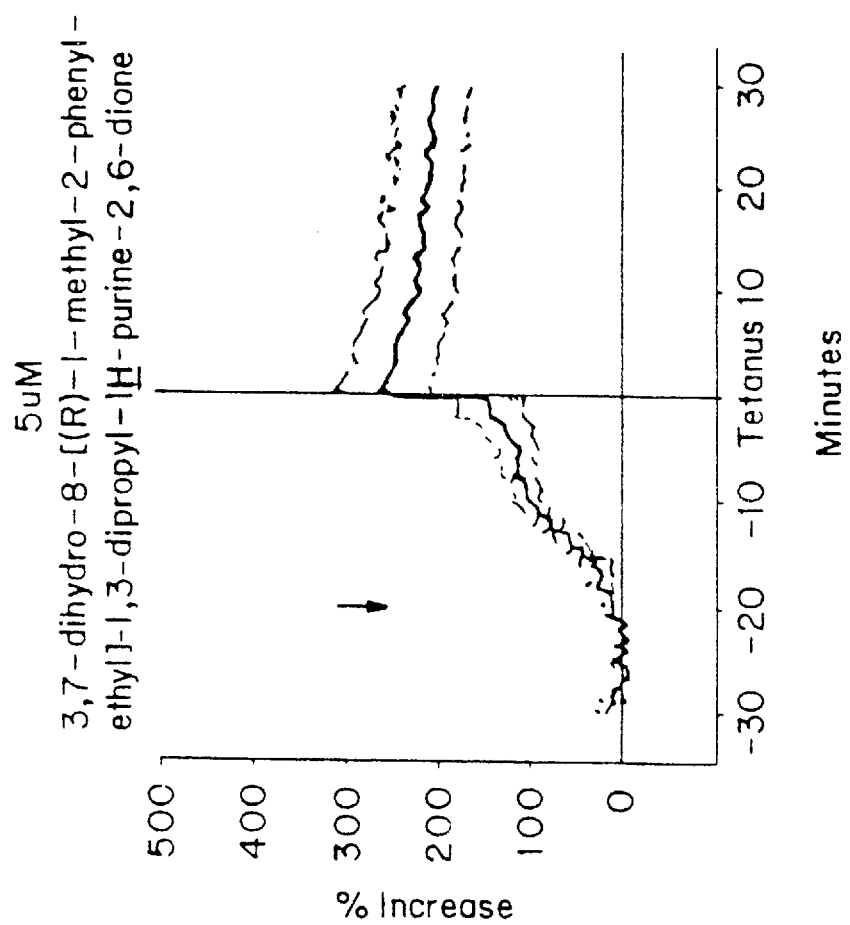

XANTHINE DERIVATIVES AS ADENOSINE A1 RECEPTOR ANTAGONISTS

This present application has an effective international filing date of Jan. 27,1994 as application PCT/US94/01009 which designated the U.S. and entered the U.S. national phase on Jul. 26, 1996 under 35 USC 371 and was assigned Ser. No. 08/500,991 and accorded a filing date of Dec. 18, 1995, which is a continuation of application Ser. No. 08/023, 501 filed on Feb. 26, 1993, now abandoned.

FIELD OF THE INVENTION

The present invention relates to a group of compounds which are xanthine derivatives and which act selectively at adenosine receptors. Adenosine antagonists acting at the $A_1$ receptor can depolarize postsynaptic neurons and can presynaptically enhance the release of a number of neurotransmitters, including acetylcholine, glutamate, serotonin, and norepinephrine, and thus have potential for treatment of cognitive deficits and for cognition-enhancing effects.

BACKGROUND OF THE INVENTION

The profound hypotensive, sedative, antispasmodic, and vasodilatory actions of adenosine were first recognized over 50 years ago. Subsequently, the number of biological roles proposed for adenosine have increased considerably. The adenosine receptors appear linked in many cells to adenylate cyclase. A variety of adenosine analogues have been introduced in recent years for the study of these receptor functions. Alkylxanthines, such as caffeine and theophylline, are the best known nonselective antagonists of adenosine receptors.

Adenosine represents a general regulatory substance, since no particular cell type or tissue appears uniquely responsible for its formation. In this regard, adenosine is unlike various endocrine hormones. Nor is there any evidence for storage and release of adenosine from nerve or other cells. Thus, adenosine is unlike various neurotransmitter substances; it appears to be a neuromodulator rather than a neurotransmitter.

Although adenosine can affect a variety of physiological functions, particular attention has been directed over the years toward actions which might lead to clinical applications. It has now been recognized that there are not one but at least two classes of extracellular receptors involved in the action of adenosine. One of these has a high affinity for adenosine and at least in some cells couples to adenylate cyclase in an inhibitory manner. These have been termed the $A_1$ receptors. The other class of receptors has a lower affinity for adenosine and in many cell types couples to adenylate cyclase in a stimulatory manner. These have been termed the $A_2$ receptors.

The adenosine analogues exhibit differing rank orders of potencies at $A_1$ and $A_2$ adenosine receptors, providing a simple method of categorizing a physiological response with respect to the nature of the adenosine receptor. The blockade of adenosine receptors (antagonism) provides another method of categorizing a response with respect to the involvement of adenosine receptors.

Adenosine in the central nervous system (CNS) acts as a neuromodulator exerting its effects via the $A_1$ and $A_2$ receptors (G. L. Stiles, TIPS, 12, 486 (1986)). The majority of adenosine receptors is localized in the brain, where $A_2$ receptors are found in the striatum, while $A_1$ receptors predominate in the hippocampus and in the cortex (areas involved in learning and memory). In general terms, $A_1$ receptors cause an inhibition of the release of excitatory as well as of inhibitory neurotransmitters and a postsynaptic decrease of excitability. These effects are G-protein dependent, and they are mediated by an inhibition of adenylate cyclase and of calcium influx and by an increase in potassium efflux (B. B. Fredholm, et al., TIPS, 9, 130 (1988)). In turn, $A_1$ antagonists can be expected to depolarize postsynaptic neurons and to presynaptically enhance the release of various neurotransmitters (e.g. acetylcholine, glutamate, serotonin, and norepinephrine). This action could be of value in treating cognitive deficits such as those associated with Alzheimer's disease, as these transmitters have been implicated in learning and memory, and each of these transmitters is reduced in Alzheimer's disease.

In view of the above, the compounds disclosed herein would be useful as agents for the treatment of cognitive deficit disorders and conditions.

SUMMARY OF THE INVENTION

The present invention relates to compounds having the following general structures:

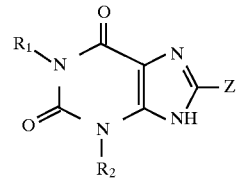

including the (R) and (S) enantiomers and racemic mixtures thereof, and the pharmaceutically acceptable salts thereof, wherein $R_1$ and $R_2$ are each independently $(C_1-C_4)$lower alkyl or $(C_2-C_4)$lower alkenyl, Z is:

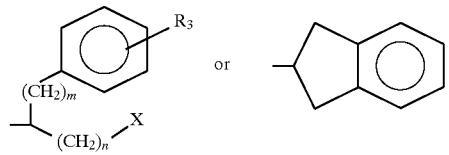

$R_3$ is $(C_1-C_3)$lower alkyl, nitro, amino, hydroxy, fluoro, bromo or chloro, m is zero or an integer from 1 to 4, n is an integer from 1 to 4, and X is H or OH.

As used in this application the term $(C_1-C_3)$lower alkyl refers to methyl, ethyl, n-propyl, or isopropyl. Also, as used in this application the term $(C_1-C_4)$lower alkyl refers to methyl, ethyl, n-propyl, isopropyl, n-butyl, isobutyl, sec-butyl or tert-butyl.

In addition as used in this application the term $(C_2-C_4)$ lower alkenyl refers to ethynyl, propenyl, isopropenyl, butenyl, isobutenyl, etc.

Also, as used in this application, the substituent represented by $R_3$ may be at any position from 2–6 around the phenyl ring. There may be up to three such independent substitutions around the ring wherein the substituent is other than hydrogen.

Using a novel synthetic approach based on a unique binding mode proposed for xanthines at adenosine receptors, several 8-substituted xanthines have been synthesized. One of these compounds, 3,7-dihydro-8[(R)-1-methyl-2-phenylethyl], 1,3-dipropyl-1H-purine-2,6-dione is a potent, selective adenosine $A_1$ receptor antagonist based on displacement binding studies in rat brain ($A_1$ receptor Ki, 6.9 nM; $A_2$ receptor Ki, 157 nM). 3,7-dihydro-8[(R)-1-methyl-2- phenyl-ethyl]1, 3-dipropyl-1H-purine-2,6-dione had little effect on Type III or Type IV phosphodiesterase activity. In the anesthetized guinea pig, 3,7-dihydro-8-[(R)-methyl-2-phenylethyl]1, 3-dipropyl-1H-purine-2,6-dione completely reversed the $A_1$ receptor mediated decrease in heart rate produced by adenosine. In isolated guinea pig trachea, 3,7-dihydro-8[(R)-1-methyl-2-phenylethyl]1,3-dipropyl-1H-purine-2,6-dione had very little effect on contraction produced by $N^6$-cyclohexyl-adenosine, an $A_1$ selective agonist. These observations suggest that multiple $A_1$ receptor subtypes may exist peripherally (Secrest, et al., *FASEB Journal*, 6, 1992).

We have now discovered, using the methods described in more detail below, that the above compounds are useful as cognition enhancing agents and, therefore, that the compounds are useful in the treatment of conditions characterized by the exhibition of cognitive deficits.

3,7-Dihydro-8-[(R)-1-methyl-2-phenylethyl]1,3-dipropyl-1H-purine-2,6-dione and (R)-1,3-dipropyl-8-(1-phenyl-propyl)-xanthine [aka 3,7-dihydro-8-[(R)-1-phenylpropyl]1,3-dipropyl-1H-purine-2,6-dione] are potent and selective $A_1$ antagonists (Dudley et al., *Soc. Neurosci. Abstr.*, 1992; Secrest, et al.). These compounds have been tested in models of learning and memory both in vitro (hippocampal long-term potentiation) and in vivo (water maze learning).

Long-term potentiation (LTP) in the hippocampal slice has been suggested as a model for events that might occur at a cellular level during learning and memory processes. (R)-1,3-dipropyl-8-(1-phenylpropyl)-xanthine and 3,7-dihydro-8[(R)-1-methyl-2-phenylethyl]1,3-dipropyl-1H-purine-2,6-dione increased the basal population spike before and after induction of LTP recorded in hippocampal CA1 neurons. Similar results were found with another $A_1$ antagonist, KFM-19.

In the water maze spatial learning model, rats are required to use distal spatial cues around a circular water tank to navigate to a hidden platform. The cholinergic antagonist scopolamine dose-dependently impairs acquisition of the water maze task. (R)-1,3-dipropyl-8-(1-phenylpropyl)-xanthine, 3,7-dihydro-8[(R)-1-methyl-2-phenylethyl]1,3-dipropyl-1H-purine-2,6-dione, and KFM-19 significantly antagonized the scopolamine-induced learning impairment.

These results (detailed below) indicate that the adenosine $A_1$ antagonists (R)-1,3-dipropyl-8-(1-phenyl-propyl)-xanthine and 3,7-dihydro-8[(R)-1-methyl-2-phenyl-ethyl]1, 3-dipropyl-1H-purine-2,6-dione have potential cognition-enhancing effects both in vitro and in vivo. (R)-1,3-Dipropyl-8-(1-phenylpropyl)-xanthine and 3,7-dihydro-8[(R)-1-methyl-2-phenylethyl]1,3-dipropyl-1H-purine-2,6-dione, thus also have potential as a treatment for cognitive deficits.

Figure 1:
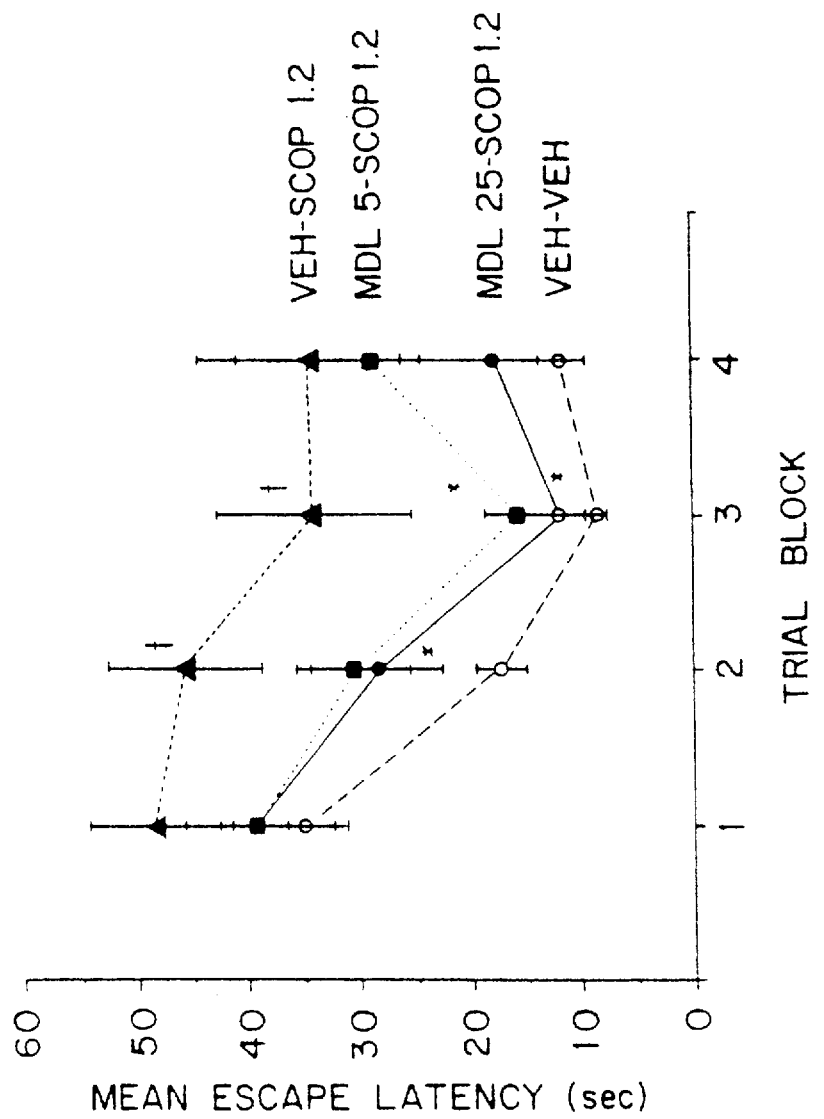
FIG. 1

Shows effect of (R)-1,3-dipropyl-8-(1-phenylpropyl)-xanthine on scopolamine-induced impariment of water maze learning, showing the mean latency (±s.e.m.) to locate the platform over blocks of three trials of groups which receive vehicle plus vehicle (VEH—VEH), vehicle plus scopolamine at 1.2 mg/kg (VEH-SCOP 1.2), (R)-1,3-dipropyl-8-(1-phenylpropyl)-xanthine at 5 mg/kg plus scopolamine at 1.2 mg/kg (MDL 5-SCOP 1.2), or (R)-1,3-dipropyl-8-(1-phenylpropyl)-xanthine at 25 mg/kg plus scopolamine at 1.2 mg/kg (MDL 25-SCOP 1.2). † indicates significant difference from VEH—VEH group; * indicates significant difference from VEH-SCOP 1.2 group.

FIG. 2

Shows effect of 3,7-dihydro-8-[(R)-1-methyl-2-phenylethyl]-1,3-dipropyl-1H-purine-2,6-dione on scopolamine-induced impairment of water maze learning, showing the mean latency (±s.e.m.) to locate the platform over blocks of three trials of groups which receive vehicle plus vehicle (VEH—VEH), vehicle plus scopolamine at 1.5 mg/kg (VEH-SCOP 1.5), or 3,7-dihydro-8-[(R)-1-methyl-2-phenylethyl]-1,3-dipropyl-1H-purine-2,6-dione at 25 mg/kg plus scopolamine at 1.5 mg/kg (MDL 25-SCOP 1.5). "*" indicates significant difference from VEH—VEH group.

FIG. 3a

Shows the percentage increase in the basal pop spike in rat brain slices versus time before and after induction of a "primed burst" following vehicle [DMSO] exposure.

FIG. 3b

Shows the percentage increase in the basal pop spike in rat brain slices versus time before and after induction of a "primed burst" following drug [(R)-1,3-dipropyl-8-(1-phenylpropyl)-xanthine] exposure.

FIG. 3c

Shows the percentage increase in the basal pop spike in rat brain slices versus time before and after induction of a "primed burst" following drug [3,7-dihydro-8-[(R)-1-methyl-2-phenylethyl]-1,3-dipropyl-1H-purine-2,6-dione] exposure.

DETAILED DESCRIPTION OF THE INVENTION

Receptor Binding

The following methods were used to examine represenative compounds as disclosed herein for their $A_1$ and $A_2$ receptor-binding affinity.

Methods $A_1$ Receptor Affinity

The test described below was used to determine the potency of test compounds to compete with the ligand [$^3$H]cyclohexyladenosine for the adenosine $A_1$ receptor prepared from rat brain membranes. Male Sprague-Dawley rats were sacrificed by decapitation and the membranes were isolated from whole animal brains. See R. Goodman, et al., *Guanine Nucleotide and Cation Regulation of the Binding of [3H] Diethylphenylxanthine to Adenosine A-1 Receptors in Brain Membrane, Molecular Pharmacology*, 21, 329–335 (1982).

Membranes were homogenized (using polytron setting 7 for 10 seconds) in 25 volumes of ice-cold 50 mM Tris-HC1 buffer, pH 7.7. The homogenate was centrifuged at 19,000 rpm for 10 minutes at 4° C. The pellet was washed by resuspending in 25 volumes of buffer with 2 IU of adenosine deaminase per ml and incubated 30 minutes at 37° C. The homogenate was centrifuged again. The final pellet was resuspended in 25 volumes of ice-cold buffer.

The incubation tubes, in triplicate, received 100 μl of [$^3$H]cyclohexyladenosine, 0.8 nM in the assay, 200 μl of test compounds at various concentrations over the range of $10^{-10}$ M to $10^{-6}$ M diluted with 50 nM Tris-HC1 buffer (pH 7.7), 0.2 ml of membrane suspension (8 mg wet weight) and in a final volume of 2 ml with Tris buffer. Incubations were carried out at 25° C. for 2 hours and each one was terminated within 10 seconds by filtration through a GF/B glass fiber filter using a vacuum. The membranes on the filters were transferred to scintillation vials. The filters were counted by liquid scintillation spectrometry in 8 ml of Omniflour containing 5% Protosol.

Specific binding of [$^3$H]cyclohexyladenosine was measured as the excess over blanks taken in the presence of $10^{-5}$ M 2-chloroadenosine. Total membrane-bound radioactivity was about 5% of that added to the test tubes. Specific binding to membranes was about 90% of the total bound. Protein content of the membrane suspension was determined by the method of O. H. Lowry, et al., *Protein Measurements With Folin Phenol Reagent, J. Biol. Chem.*, 193, 265–275 (1951).

Displacement of [$^3$H]cyclohexyladenosine binding of 15% or more by a test compound was indicative of affinity for the adenosine binding site.

$A_2$ Receptor Affinity

The test described below was used to determine the potency of test compounds to compete with the ligand [$^3$H]5'-N-ethyl-carboxamidoadenosine (NECA) for the adenosine $A_2$ receptors prepared from animal brain membranes. See R. R. Bruns, et al., *Characterization of the A-2Adenosine Receptor Labeled by [3H]NECA in Rat Striatal Membranes, Mol. Pharmacol.*, 29, 331–346 (1986). Young male rats (C-D strain), obtained from Charles River, were killed by decapitation and the brain was removed. Membranes for ligand binding were isolated from rat brain striatum. The tissue was homogenized in 20 vol ice-cold 50 mM Tris-HC1 buffer (pH 7.7) using a polytron (setting for 6 to 20 seconds). The homogenate was centrifuged at 50,000×g for 10 minutes at 4° C. The pellet was again homogenized in a polytron in 20 vol of buffer, and centrifuged as before. The pellet was finally resuspended in 40 vol of 50 mM Tris-HC1 (pH 7.7) per gram of original wet weight of tissue.

Incubation tubes, in triplicate, received 100 μl of [3H] NECA (94 nM in the assay), 100 μl of 1 μM cyclohexyladenosine (CHA), 100 μl of 100 mM $MgCl_2$, 100 μl of 1 IU/ml adenosine deaminase, 100 μl of test compounds at various concentrations over the range of $10^{-10}$M to $10^{-4}$M diluted with assay buffer (50 mM Tris-HC1, pH 7.7) and 0.2 μl of membrane suspension (5 mg wet weight), in a final volume of 1 ml of 50 mM Tris-HC1, pH 7.7. Incubations were carried out at 25° C. for 60 minutes. Each tube was filtered through GF/B glass fiber filters using a vacuum. The filters were rinsed two times with 5 ml of the ice-cold buffer. The membranes on the filters were transferred to scintillation vials to which 8 ml of Omnifluor with 5% Protosol was added. The filters were counted by liquid scintillation spectrometry.

Specific binding of [$^3$H]NECA was measured as the excess over blanks run in the presence of 100 μM 2-chloroadenosine. Total membrane-bound radioactivity was about 2.5% of that added to the test tubes. Since this condition limits total binding to less than 10% of the radioactivity, the concentration of free ligand does not change appreciably during the binding assay. Specific binding to membranes was about 50% of the total bound. Protein content of the membrane suspension was determined by the method of Lowry, et al.

Displacement of [$^3$H]NECA binding of 15% or more by a test compound was indicative of affinity for the adenosine $A_2$ site. The molar concentration of a compound which causes 50% inhibition of the binding of ligand was the $IC_{50}$. A value in the range of 100–1000 nM would indicate a highly potent compound.

Results

The following Table 1 shows the adenosine receptor binding affinities for several compounds.

TABLE 1

| Adenosine Receptor Binding Affinity | | | |
|---|---|---|---|
| | $A_1$ Ki | $A_2$ Ki | $A_2/A_1$ |
| 3,7-Dihydro-8-[(S)-1-methyl-2-phenylethyl]-1,3-dipropyl-1H-purine-2,6-dione | 60.7 nm | 848 nm | 14 |
| 3,7-Dihydro-8-[(±)-1-methyl-2-phenylethyl]-1,3-dipropyl-1H-purine-2,6-dione | 32.6 nm | 644 nm | 20 |
| 3,7-Dihydro-8-[(R)-1-methyl-2-phenylethyl]-1,3-dipropyl-1H-purine-2,6-dione | 6.9 nm | 157 nm | 23 |
| 3,7-Dihydro-8-[(S)-1-phenyl-ethyl]-1,3-dipropyl-1H-purine-2,6-dione | 174.7 nm | 12,900 nm | 74 |
| 3,7-Dihydro-8-[(±)-1-phenyl-ethyl]-1,3-dipropyl-1H-purine-2,6-dione | 49.4 nm | 4,900 nm | 99 |
| 3,7-Dihydro-8-[(R)-1-phenyl-ethyl]-1,3-dipropyl-1H-purine-2,6-dione | 25.3 nm | 4,220 nm | 160 |
| 3,7-Dihydro-8-[(±)-1-phenyl-methyl)propyl]-1,3-dipropyl-1H-purine-2,6-dione | 161.2 nm | 1,230 nm | 8 |
| 3,7-Dihydro-8-[(±)-1-(phenyl-methyl)butyl]-1,3-dipropyl-1H-purine-2,6-dione | 73.8 nm | 610 nm | 8 |
| 3,7-Dihydro-8-[(±)-1-(2-indanyl]-1,3-dipropyl-1H-purine-2,6-dione | 64.3 nm | 8,350 nm | 129 |
| 3,7-Dihydro-8-[(±)-hydroxy-methyl-2-phenylethyl]-1,3-dipropyl-1H-purine-2,6-dione | 1,294 nm | 12,800 nm | 10 |
| 3,7-Dihydro-8-[(±)-phenyl-propyl]-1,3-dipropyl-1H-purine-2,6-dione | 32.6 nm | 644 nm | 20 |
| 3,7-Dihydro-8-[(R)-phenyl-propyl]-1,3-dipropyl-1H-purine-2,6-dione {aka (R)-1,3-dipropyl-8-(1-phenylpropyl)-xanthine} | 23.2 nm | 3,510 nm | 153 |
| 3,7-Dihydro-8-[(S)-phenyl-propyl]-1,3-dipropyl-1H-purine-2,6-dione | 60.7 nm | 848 nm | 14 |
| 3,7-Dihydro-8-[(±)-2-phenyl-propyl]-1,3-dipropyl-1H-purine-2,6-dione | 94.3 nm | 1,740 nm | 18 |
| 3,7-Dihydro-8-[(±)-trans-2-phenylcyclopentyl]-1,3-dipropyl-1H-purine-2,6-dione | 164.3 nm | 2,720 nm | 10 |
| 3,7-Dihydro-8-[(±)-1,2,3,4-tetrahydro-2-naphthalenyl-1H-purine-2,6-dione | 94.6 nm | 10,300 nm | 108 |

Cognition-Enhancing Effects

The following methods were used to examine representative compounds as disclosed herein for their cognition-enhancing effects. The compounds were tested in animal models of learning and memory both in vitro (hippocampal long-term potentiation) and in vivo (water maze learning).

Water Maze Learning Methods

Training

Rats were trained in a 120 -cm diameter water-filled tank to locate a hidden platform submerged just below the surface of the water. The location of the platform remained constant, but for each trial, the animal was required to swim from one of three different starting locations around the edge of the tank. There were no proximal cues in the tank, so the animal had to use a spatial mapping strategy using the distal cues around the room to navigate to the hidden platform. A computerized video tracking system allowed automated acquisition of the data. The animals were given 12 successive training trials during the single training day, using the methods of O. Buresova, et al., *Differential Effects Of Cholinergic Blockade On Performance Of Rats In The Water Tank Navigation Task And In A Radial Water Maze, Behavioral Neuroscience*, 100, 476–482 (1986). Each trial had a maximum duration of sixty seconds. If the animal did not locate the platform by that time, it was placed on the platform. After the animal found or was placed on the platform, it was allowed to stay there for 30 seconds. The next trial commenced immediately following the 30 second stay on the platform. Latency to locate the platform was recorded for each trial.

Drug Administration

Separate treatment groups of five animals each were run in each experiment. The VEH—VEH groups received vehicle (distilled water plus Tween) i.p. 40 minutes prior to the first trial and vehicle i.p. 20 min. prior to the first trial. The VEH-SCOP groups received vehicle i.p. at 40 minutes and scopolamine HBr i.p. at 20 minutes. The MDL-SCOP groups received (R)-1,3-dipropyl-8-(1-phenylpropyl)-xanthine or 3,7-dihydro-8[(R)-1-methyl-2-phenylethyl]1,3-dipropyl-1H-purine-2,6-dione i.p. at 40 minutes and scopolamine HBr i.p. at 20 minutes.

Data analysis

The latency scores for each animal were averaged into four blocks of three trials each (one trial from each starting location). A one-way ANOVA comparing the treatment groups was computed on the scores for each trial block. If the overall ANOVA was statistically significant, comparisons between individual treatment groups were made with Fisher's PLSD test.

Results And Discussion (R)-1,3-Dipropyl-8-(1-Phenylpropyl)-Xanthine

The selective $A_1$ antagonist (R)-1,3-dipropyl-8-(1-phenylpropyl)-xanthine reversed the scopolamine-induced impairment at 5 and 25 mg/kg i.p., as shown in FIG. 1. The overall ANOVAs for blocks 2 and 3 were significant, F(3, 16)=4.861, p<0.02, and F (3,16)=4.219, p=0.02. Individual comparisons indicated that the VEH-SCOP group differed significantly from the VEH—VEH group (p<0.05), and the MDL-SCOP groups did not differ significantly from the VEH—VEH group. In addition, the MDL 5-SCOP group differed from the VEH-SCOP group on block 3 (p<0.05), and the MDL 25-SCOP group differed from the VEH-SCOP group on blocks 2 and 3.

3,7-Dihydro-8[(R)-1-methyl-2-phenylethyl]1,3-dipropyl-1H-purine-2,6-dione

Figure 2:
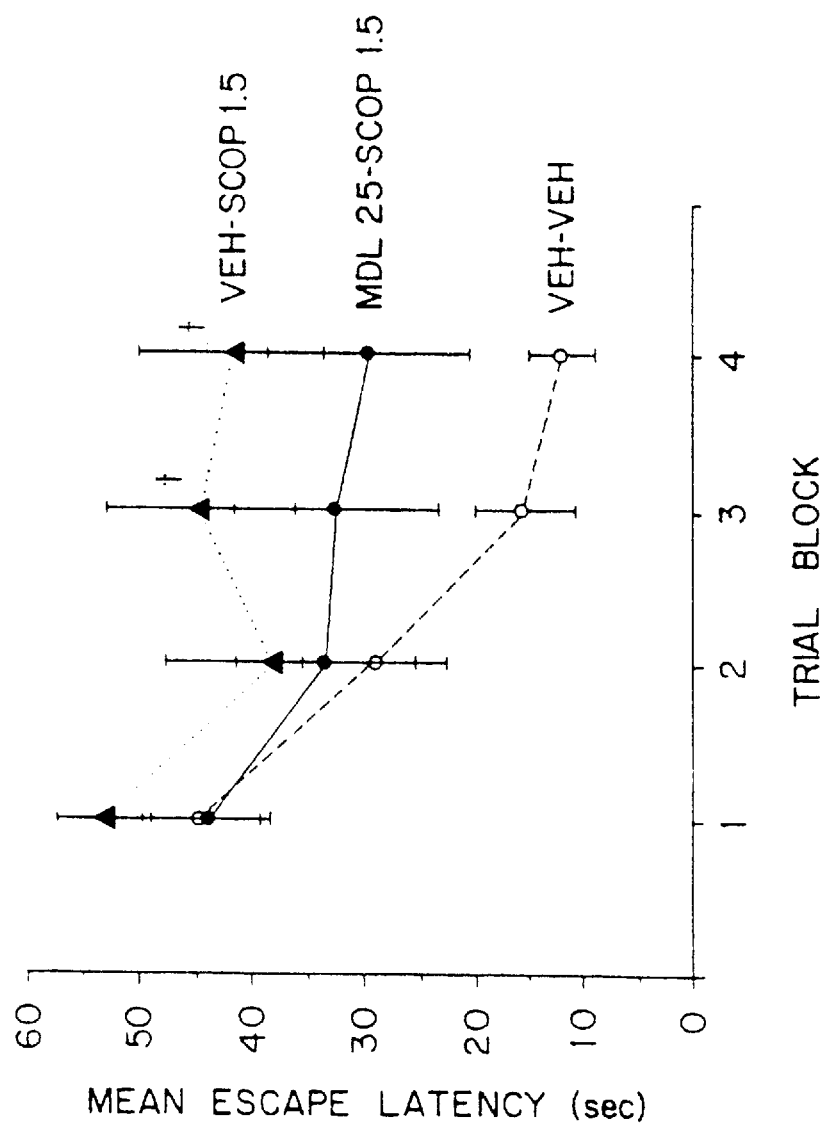

The selective $A_1$ antagonist 3,7-dihydro-8[(R)-1-methyl-2-phenylethyl]1,3-dipropyl-1H-purine-2,6-dione partially reversed the scopolamine-induced impairment of water maze learning at 25 mg/kg i.p., as shown in FIG. 2. The overall ANOVAs for blocks 3 and 4 were significant, F (2,13)=4.184, p<0.05, and F (2,13)=4.881, p<0.05. Individual comparisons indicated that the VEH-SCOP group differed significantly from the VEH-VEH group (p<0.05), and the MDL-SCOP group did not differ significantly from the VEH—VEH group.

These results indicate that (R)-1,3-dipropyl-8-(1-phenylpropyl)-xanthine and 3,7-dihydro-8[(R)-1-methyl-2-phenylethyl]1,3-dipropyl-1H-purine-2,6-dione have potential cognition-enhancing effects and could be used to treat cognitive deficits.

We have obtained similar results in the water maze test with the selective $A_1$ antagonist KFM-19 (Boehringer Ingelheim), which has been reported to have activity in other animal models of learning and memory (G. Schingnitz, et al., *Selective $A_1$-Antagonists For Treatment Of Cognitive Deficits, Nucleosides & Nucleotides*, 10(5), 1067–76 (1991)).

Hippocampal Long-Term Potentiation Methods

In Vitro Hippocampal Slice

Slices were prepared from male Sprague-Dawley rats. Slice preparation techniques were modified from A. L. Mueller, et al., *Noradrenergic Responses In Rat Hippocampus:Evidence For Mediation By Alpha and Beta Receptors In The In Vitro Slice, Brain Res.*, 214, 113–26 (1981). Briefly, the hippocampus was rapidly and gently dissected over ice. 400 $\mu$ Sections were made with a MacIlwain tissue chopper and incubated on the interface of 34° C. Kreb's buffer (124 mM NaCl; 4.9 mM $KH_2PO_4$; 2.4 mM $MgSO_4$; 2.5 mM. $CaCl_2$; 25.6 mM NaHCO3; 10 mM glucose) for at least one hour. Warm, moist 95% $O_2$/5% $CO_2$ was passed over the incubation chamber. To record, a slice was submerged in warmed, oxygenated media flowing at 2 ml/min.

Recording

A recording electrode was placed in the CA1 region of the hippocampus and a stimulating electrode was positioned in the stratum radiatum of the CA3 region of this same slice. The bipolar stimulating electrode was made from a twisted pair of 62 $\mu$ nichrome wires. 100 $\mu$sec pulses were applied at 30 second intervals and a glass recording electrode, 1–2 M$\Omega$ impedance, filled with 3 M NaCl was used to carry the resultant CA1 population spike. The signal form the CA1 cell body layer was amplified, filtered (1 Hz-4 KHz), and monitored on an oscilloscope. The evoked waveform was also digitized using a Computerscope A/D board (RC Electronics, Inc., Santa Barbara, Calif.) and stored for analysis using Neuroscope software (Levin and Associates, Denver, Colo.) running on an IBM-AT. In order to insure the viability of the slice, "minimal viability criteria" were established. First, when the stimulus voltage was adjusted to evoke a threshold population spike the maximum EPSP had to be greater than 1 mV. Also, the maximum population spike amplitude obtainable had to be greater than 5 mV. Finally, a paired pulse test was performed and a minimum paired pulse inhibition duration of at least 30 msec was established to insure the viability of inhibitory inter-neurons (P. DiSenna, *Method And Myth In Maintaining Brain Slices*, in A. Schurr, et al., Eds. *Brain Slices: Fundamentals, Applications, and Implications*, (1987) Switzerland; S. Karger AG, 10–21). Only preparations that met these three criteria were used.

Twenty or more control population spikes were obtained to establish a baseline (at least 10 minutes). In most slices concentrated drug solutions were then diluted into the media for a 20 minute period to establish effects on the baseline population spike. A "primed burst" tetanus was performed following the 20 minute drug exposure. One 100 $\mu$sec pulse was followed by 4 similar pulses 170, 180, 190, 200 msec later. Drug superfusion was continuous throughout the experiment.

Drugs Used

Seven slices received DMSO, 0.25% (vehicle controls). Six slices were given (R)-1,3-dipropyl-8-(1-phenylpropyl)-xanthine at 2.5 $\mu$m and six slices were given 3,7-dihydro-8 [(R)-1-methyl-2-phenylethyl]1,3-dipropyl-1H-purine-2,6-dione at 5 $\mu$M. The compounds were dissolved in DMSO and diluted 1:400 into the perfusion media. In our hands, this dilution of DMSO had minimal effect on the slices.

Data Analysis

Each pop spike waveform was digitized, stored, and analyzed by the Neuroscope software. Pop spike amplitude was determined for each waveform and these amplitudes were normalized to pre-tetanus levels. Results were expressed as percent change from this control level and plotted vs. time. Data from individual experiments were averaged across treatments using Lotus 123 and graphed.

Figure 3A:
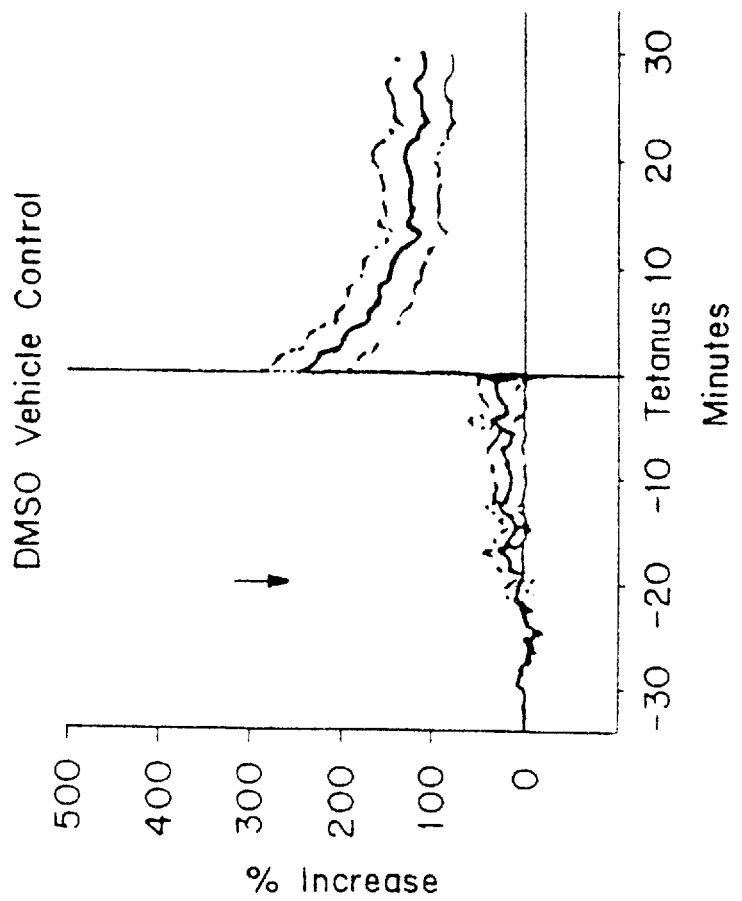

Results And Discussion 3,7-dihydro-8[(R)-1-methyl-2-phenylethyl]1,3-dipropyl-1H-purine-2,6-dione increased the basal pop spike by 133%. (R)-1,3-dipropyl-8-(1-phenylpropyl)-xanthine increased the basal pop spike by 130%. DMSO alone increased the basal spike by 7.8%. Following tetanus, the resultant LTP stabilized at 216% with 3,7-dihydro-8[(R)-1-methyl-2-phenylethyl]1,3-dipropyl-1H-purine-2,6-dione, at 270% with (R)-1,3-dipropyl-8-(1-phenylpropyl)-xanthine and at 109% with DMSO alone. In addition, the LTP with 3,7-dihydro-8[(R)-1-methyl-2-phenylethyl]1,3-dipropyl-1H-purine-2,6-dione and (R)-1,3-dipropyl-8-(1-phenylpropyl)-xanthine rose sharply and remained stable throughout the observation period. LTP in tetanized control slices rose sharply but dropped to a stable level after 10–14 minutes (see FIG. 3).

The results indicate that (R)-1,3-dipropyl-8-(1-phenyl-propyl)-xanthine and 3,7-dihydro-8[(R)-1-methyl-2-phenyl-ethyl]1,3-dipropyl-1H-purine-2,6-dione have potential as treatments for cognitive deficits. The results we obtained are similar to those reported for another $A_1$ antagonist, KFM-19 (G. Schingnitz, et al.). (R)-1,3-dipropyl-8-(1-phenylpropyl)-xanthine, 3,7-dihydro-8[(R)-1-methyl-2phenylethyl]1,3-dipropyl-1H-purine-2,6-dione, and KFM-19 all enhanced synaptic transmission in the hippocampal slice. This enhancement of synaptic transmission is indicative of the cognition enhancing potential of a compound.

The present studies indicate that the adenosine $A_1$ antagonists (R)-1,3-dipropyl-8-(1-phenylpropyl)-xanthine and 3,7-dihydro-8[(R)-1-methyl-2-phenylethyl]1, 3-dipropyl-1H-purine-2,6-dione have potential cognition-enhancing effects both in vitro and in vivo. These compounds thus have potential as a treatment for cognitive deficits.

The following Table 2 summarizes some of the potential indications for the cognition-enhancing compounds disclosed herein and illustrates some cognitive deficit improvement applications as well.

TABLE 2

POTENTIAL INDICATIONS FOR MEMORY-ENHANCING AGENT[1]

| Indication | Approximate Prevalence (1990)* |
|---|---|
| Deficit Improvement Applications | |
| Alzheimer's disease | 6.2 Million |
| Multi-infarct dementia | 4.2 Million |
| Age-associated memory impairment (senility) | 60 Million |
| Korsakoff's syndrome | 22,000 |
| Head-trauma-induced amnesia | 3.6 Million |
| Other amnesias | 600,000 |
| Down's syndrome | 600,000 |
| Attention deficit disorder | 5 Million |
| Mental retardation | 5.5 Million |
| Enhancement of Normal Function | |
| Adjunct to psychotherapy | 10–50 Million |
| Scholastic performance | 20 Million |
| Job performance | 270 Million |
| Intelligence-gathering/eyewitness accounts | 1–2 Million |

TABLE 2-continued

POTENTIAL INDICATIONS FOR MEMORY-ENHANCING AGENT[1]

| Indication | Approximate Prevalence (1990)* |
|---|---|

*In the six major markets of France, Germany, Italy, Japan, the United Kingdom, and the United States
[1]Cognos, Memory Enhancement, Decision Resource Inc., 17 New England Executive Park, Burlington, MA 01803 (June 1991)

In general, compounds according to the invention can be made by following the procedures described in detail in Reaction Schemes I and II below.

REACTION SCHEME I

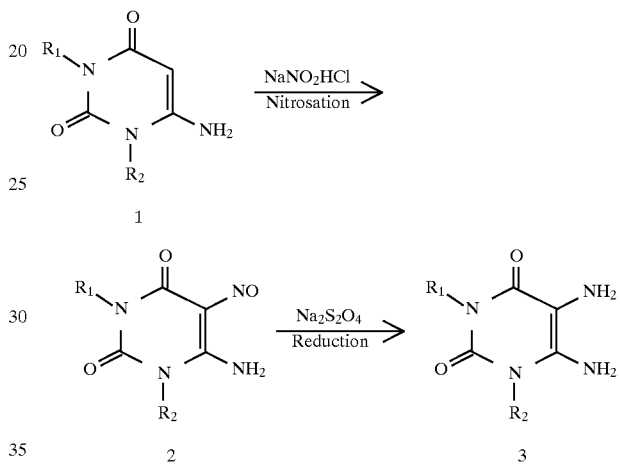

An appropriately alkyl substituted starting compound 1, 6-amino-2,4(1H,3H)-pyrimidinedione, wherein $R_1$ and $R_2$ are defined as above, is chosen so that $R_1$ and $R_2$ are defined the same as that desired in the final product.

The 6-amino-2,4(1H,3H)-pyrimidinedione is suspended in water with 20% acetic acid. Sodium nitrite (1.5 equivalents) in water is added in portions while keeping the solution mildly acidic with concentrated hydrochloric acid. The suspension is allowed to stir for several hours. It is then filtered, rinsed with water and dried under vacuum to yield the purple colored, alkyl substituted 6-amino-5-nitroso-2, 4(1H,3H)-pyrimidinedione (2).

The alkyl substituted 6-amino-5-nitroso-2,4(1H,3H)-pyrimidinedione is then suspended in water, made alkaline with 50% ammonium hydroxide (pH≈11) and treated with excess sodium dithionate until the purple color fades. The reaction is then extracted with chloroform. The organic extracts are combined and dried over anhydrous magnesium sulfate, filtered and concentrated under vacuum. The residue is purified by flash chromatography (5% to 10% methanol in chloroform). This material is then recrystallized from 10% isopropanol/hexane to yield the alkyl substituted 5,6-diamino-2,4-(1H,3H)-pyrimidinedione (3). (See J. W. Daly, J. Med. Chem., 28, 487 (1985).)

Compound 3 from Scheme I is then reacted as shown in Scheme II.

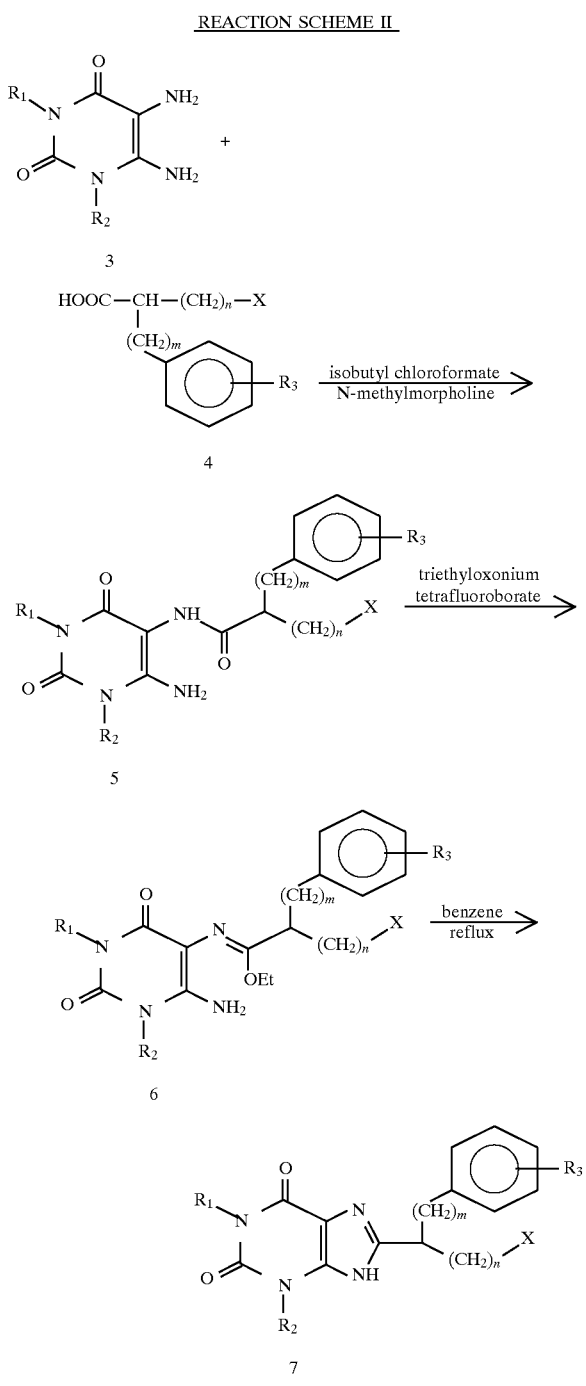

The alkyl substituted 5,6-diamino-2,4(1H,3H)-pyrimidine-dione (3) is then reacted with a 2-alkyl substituted alkanoic acid (4), wherein m, n, X and $R_3$ are defined as above. The acid (4) is chosen such that the definition of m and n are the same as that desired in the final product. It should be noted that the carbon atom designated by —CH— exhibits chirality and the acid should be chosen such that the chirality is the same as that desired in the final product. Examples of such acids include the following:
  S-(+)-2-phenylpropionic acid
  R-(-)-2-phenylpropionic acid In addition, other such acids can be prepared as follows:

$$HOOC-(CH_2)_m-CH_3 + \text{benzylchloride} = HOOC-CHX-(CH_2)_n-CH_3$$

wherein m is an integer from 1 to 4, n is m-1 and X is a benzyl group of the structure

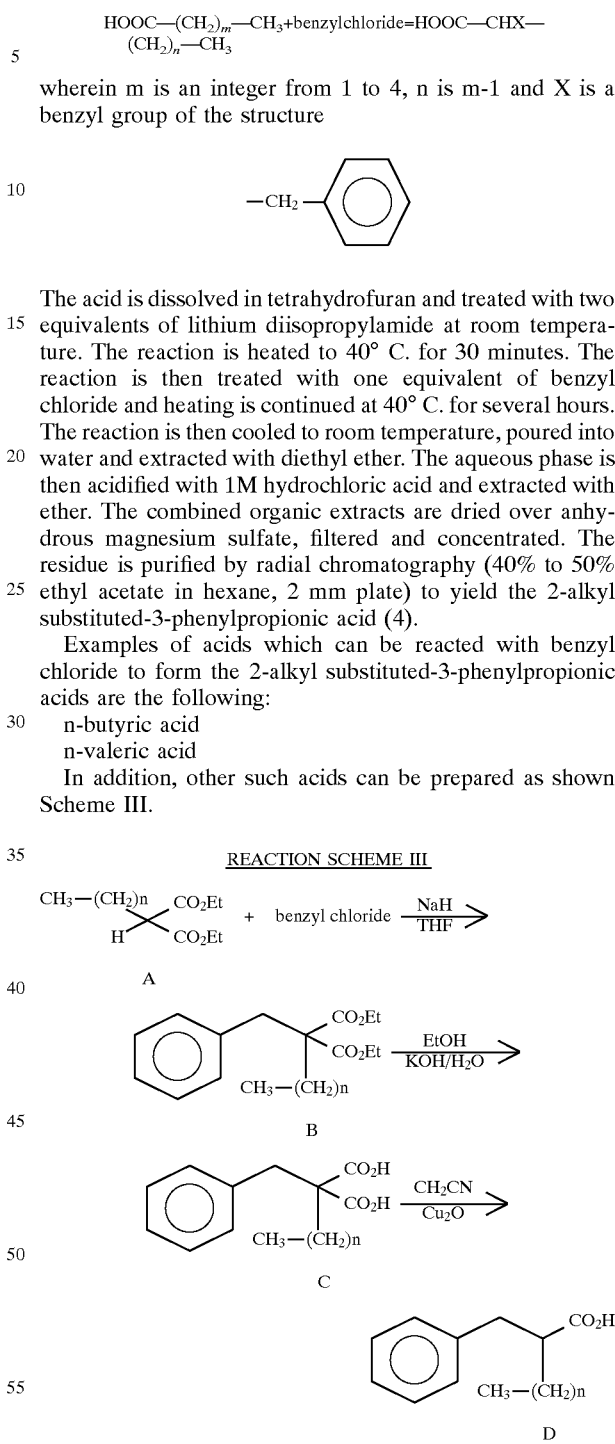

The acid is dissolved in tetrahydrofuran and treated with two equivalents of lithium diisopropylamide at room temperature. The reaction is heated to 40° C. for 30 minutes. The reaction is then treated with one equivalent of benzyl chloride and heating is continued at 40° C. for several hours. The reaction is then cooled to room temperature, poured into water and extracted with diethyl ether. The aqueous phase is then acidified with 1M hydrochloric acid and extracted with ether. The combined organic extracts are dried over anhydrous magnesium sulfate, filtered and concentrated. The residue is purified by radial chromatography (40% to 50% ethyl acetate in hexane, 2 mm plate) to yield the 2-alkyl substituted-3-phenylpropionic acid (4).

Examples of acids which can be reacted with benzyl chloride to form the 2-alkyl substituted-3-phenylpropionic acids are the following:
  n-butyric acid
  n-valeric acid In addition, other such acids can be prepared as shown Scheme III.

An appropriate alkyl substituted diethyl malonate (A), wherein n is defined as above is chosen such that n has the same definition as that desired in the final product. The malonate is added dropwise to a suspension of one equivalent of sodium hydride in tetrahydrofuran at 0° C. After stirring for approximately 30 minutes, one equivalent of benzyl chloride is added and the reaction is heated to reflux for approximately 3 hours. The reaction is then cooled, poured into water and extracted with ethyl acetate. The combined organic extracts are dried over anhydrous magnesium sulfate, filtered and concentrated under vacuum to yield the alkyl substituted diethyl benzylmalonate (B).

The alkyl substituted diethyl benzylmalonate (B) is then treated with aqueous potassium hydroxide in ethanol and heated to reflux for 14 hours. After cooling, the reaction is extracted with diethyl ether. The aqueous phase is then acidified with concentrated hydrochloric acid and extracted with diethyl ether. The combined organic extracts are dried over anhydrous magnesium sulfate and filtered and concentrated under vacuum to yield the alkyl substituted benzylmalonic acid (C).

The alkyl substituted benzylmalonic acid (C) is then dissolved in acetonitrile and treated with a catalytic amount of cuprous oxide. (See M. Maumy, et al., *Synthesis*, 15 1029 (1986).) It is then heated to reflux for 5 hours. The solvent is then removed under vacuum. The residue is taken up in diethyl ether and rinsed with 10% hydrochloric acid followed by rinsing with saturated sodium chloride solution.

to 10% methanol in chloroform)(10% to 15% isopropanol in hexane) to yield amide (5).

The amide (5) is then dissolved in dry benzene and treated with 6.5 equivalents of triethyloxonium tetrafluoroborate (1M in dichloromethane). The reaction is heated to 50° C. for approximately 2 hours. After cooling, the reaction is poured into phosphate buffer and extracted with diethyl ether. The organic phase is rinsed with saturated sodium chloride solution, dried over anhydrous magnesium sulfate, filtered and concentrated under vacuum. The residue is purified by radial chromatography (3% to 6% methanol in chloroform) to yield the imino ether (6).

The imino ether (6) is then dissolved in dry benzene and heated to reflux for approximately 2 hours under nitrogen. The solvent is removed under vacuum and the residue is purified by radial chromatography (50% ethyl acetate in hexane) to yield the 1,3-dialkyl-8-substituted xanthine (7).

REACTION SCHEME IV

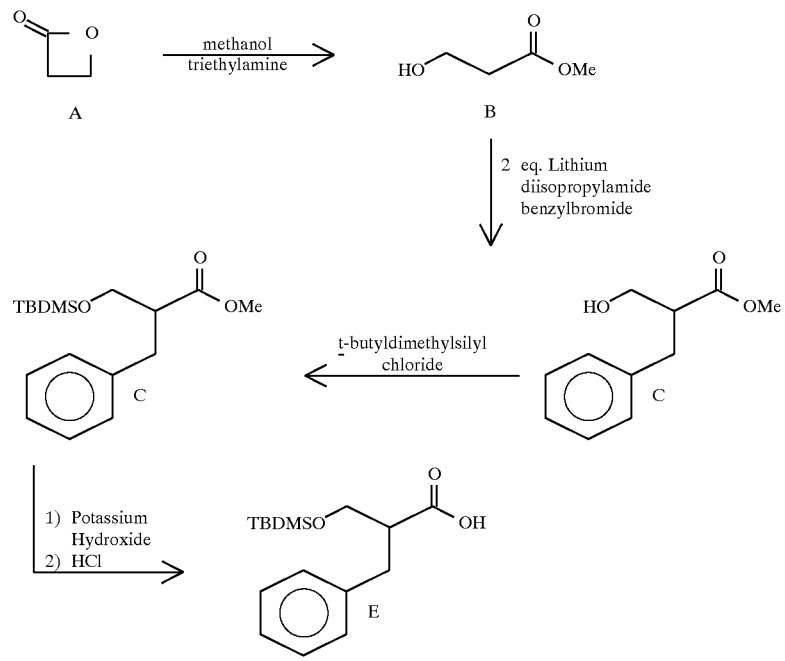

The organic extract is dried over anhydrous magnesium sulfate, filtered and concentrated under vacuum. The residue is purified by flash chromatography (5% to 10% methanol in chloroform) to yield the 2-alkyl substituted-3-phenylpropionic acid (4) (see Reaction Scheme II).

The 2-alkyl substituted-3-phenylpropionic acid (4) is then dissolved in tetrahydrofuran, treated with one equivalent of N-methylmorpholine (NMM) and cooled to −20° C. One equivalent of isobutyl chloroformate is added and the reaction is allowed to stir for approximately 30 minutes. The alkyl substituted 5,6-diamino-1,3-dipropyluracil (3) in dimethylformamide is added and the reaction is stirred at −20° C. for 4 hours. After warming to room temperature, the solvent is removed under vacuum. The residue is taken up in chloroform and rinsed with saturated sodium bicarbonate solution, followed by rinsing with saturated sodium chloride solution. The organic extract is then dried over anhydrous magnesium sulfate, filtered and concentrated under vacuum. The residue is purified by radial chromatography (3% to 5%

Another 2-subsituted alkanoic acid can be prepared as shown in Reaction Scheme IV above.

β-Propiolactone (A) is dissolved in methanol and treated with 1 equivalent of triethylamine to produce methyl 3-hydroxypropionate (B). Compound B is converted to the dianion with 2 equivalents of lithium diisopropylamide and alkylated with 1 equivalent of benzyl bromide to produce methyl 2-benzyl-3-hydroxypropionate (C). Compound C is protected as the t-butyldimethylsilyl ether (D). Compound D is then saponified with potassium hydroxide and carefully acidified to produce the acid (E). The acid (E) is then dissolved in tetrahydrofuran, treated with 1 equivalent of N-methylmorpholine and cooled to −20° C. One equivalent of isobutyl chloroformate is added, followed by 1 equivalent of 5,6-diamino-1,3-dipropyluracil in dimethyl-formamide to produce the amide. The amide is then treated with aqueous potassium hydroxide at 70° C. to produce the cyclized, deprotected 3,7-dihydro-8[(R)-1-methyl-2-phenyl-ethyl]1,3-dipropyl-1H-purine-2,6-dione.

REACTION SCHEME V

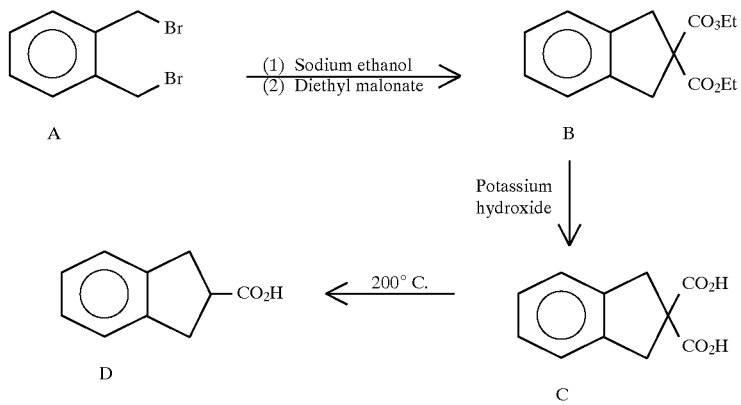

Another carboxylic acid which can be employed for the reparation of target compounds as illustrated in Reaction Scheme II can be prepared as shown in Reaction Scheme V above.

α,α-Dibromo-o-xylene (A) is treated with the anion of diethylmalonate at reflux to produce the diester (B). Compound B is then saponified with aqueous potassium hydroxide to produce compound C which is thermally decarboxylated at 200° C. to produce the indan-2-carboxylic acid (D) (J. Med. Chem., 32, 1989 (1989)). The acid (C) is then dissolved in tetrahydrofuran, treated with 1 equivalent of N-methylmorpholine, and cooled to −20° C. One equivalent of isobutyl chloroformate is added, followed by 1 equivalent of 5,6-diamino-1, 3-dipropyluracil in dimethylformamide to produce the amide. The amide is treated with aqueous potassium hydroxide and heated to reflux to produce the cyclized product, 3,7-dihydro-8-(2-indanyl)-1,3-dipropyl-1H-purine-2,6-dione.

The following list illustrates compounds according to present invention:

3,7-Dihydro-8-[(R)-1-methyl-2-phenylethyl]-1,3-dipropyl-1H-purine-2,6-dione 3,7-Dihydro-8-[(S)-1-methyl-2-phenylethyl]-1,3-dipropyl-1H-purine-2,6-dione 3,7-Dihydro-8-[(R)-1-phenylethyl]-1,3-dipropyl-1H-purine-2,6-dione 3,7-Dihydro-8-[(S)-1-phenylethyl]-1,3-dipropyl-1H-purine-2,6-dione 3,7-Dihydro-8-[1-(phenylmethyl)butyl]-1,3-dipropyl-1H-purine-2,6-dione 3,7-Dihydro-8-(1-phenylethyl)-1,3-di-2-propenyl-1H-purine-2,6-dione 3,7-Dihydro-8-[1-(phenylmethyl)propyl]-1,3-dipropyl-1H-purine-2,6-dione 3,7-Dihydro-8-(1-phenylethyl)-1,3-dipropyl-1H-purine-2,6-dione.

3,7-Dihydro-8-(1-phenylethyl-2-phenylethyl)-1,3-dipropyl-1H-purine-2,6-dione.

3,7-Dihydro-8-( 2-indanyl)-1,3-dipropyl-1H-purine-2,6-dione.

3,7-Dihydro-8-(hydroxymethyl-2-phenylethyl)-1,3-dipropyl-1H-purine-2,6-dione.

3,7-Dihydro-8-[(R)-1-phenylpropyl]1,3-dipropyl-1H-purine-2,6-dione.

3,7-Dihydro-8-[(S)-1-phenylpropyl]1,3-dipropyl-1H-purine-2,6-dione.

Pharmaceutical Preparations of the Adenosine Receptor Agents

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the breakup and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the esthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly (ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agents and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, and alkyl pyridinium halides; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quaternary ammonium salts, as well as mixtures. Alternatively, the compounds of this invention can be administered by aerosolization with a suitable carrier directly into the nasal passages, or by the administration of droplets of a solution of the compounds of this invention, in an appropriate solvent, directly into the nasal passages.

The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a nonionic surfactant having a hydrophile-lipophile balance (HLB) of from about 12 to about 17. The quantity of surfactant in such formulations LO ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The exact amount of the compound or compounds to be employed, i.e., the amount of the subject compound or compounds sufficient to provide the desired effect, depends on various, factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 $\mu$g or less to 500 mg of the active compound per ml of carrier to about 99% by weight of the active compound in combination with a pharmaceutically-acceptable carrier.

The compounds may also be incorporated into any inert carrier so that they may be utilized in routine serum assays, blood levels, urine levels, etc., according to techniques well known in the art.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as *Remington's Pharmaceutical Manufacturing*, 13 Ed., Mack Publishing Co., Easton, Pa. (1965).

The following examples are presented to illustrate the present invention but they should not be construed as limiting in any way.

EXAMPLE 1

1,3-Di-n-propyl-6-aminouracil (30 g) was suspended in 1 L of water with 41 ml of 20% acetic acid and overhead stirring. Sodium nitrite (9.03 g) in 41 ml of water was added in portions, keeping the solution acidic with 12 ml concentrated hydrochloric acid. A purple precipitate formed. Addition was complete in 10 minutes and the suspension was allowed to stir for 2 hours. The solution was then filtered, and the filtrate was rinsed with water and dried under vacuum to yield 46 g of 1,3-di-n-propyl-5-nitroso-6-aminouracil.

The 1,3-di-n-propyl-5-nitroso-6-aminouracil (61.6 g) was suspended in 1 L of water, and the suspension was made alkaline to pH 11 with 50% ammonium hydroxide and treated with 100 g of sodium dithionite, in portions, until the purple color faded. The aqueous mixture was extracted with chloroform (8×200 ml), dried over magnesium sulfate, filtered and concentrated. The residue was purified by flash chromatography (5/10% methanol/chloroform) and recrystallized from 10% isopropanol in hexane and recrystallized from 10% isopropanol to yield 37.29 g of 1,3-di-n-propyl-5,6-diaminouracil, m.p., 127°–128° C.

Sodium hydride (50% suspension in mineral oil, 15.2 g) was rinsed with 100 ml of tetrahydrofuran and suspended in 300 ml of tetrahydrofuran, cooled to 0° C. and 50 g diethyl methylmalonate dissolved in 75 ml of tetrahydrofuran was added dropwise over 45 minutes. After stirring for an additional 30 minutes, 36.8 ml of benzyl chloride was added, followed by 24 ml of tetrahydrofuran. The reaction was then heated to gentle reflux for 3 hours, cooled, poured into 400 ml of water and extracted with ethyl acetate (3×500 ml). The combined organic extracts were dried over magnesium sulfate, filtered and concentrated to yield 75 g of diethyl benzylmethylmalonate.

The diethyl benzylmethylmalonate (75 g) was combined with 300 ml of ethanol and a solution of 100 g potassium hydroxide in 300 ml of water and heated to a gentle reflux for 5 hours. After cooling, the mixture was extracted with diethyl ether (2×300 ml). The aqueous phase was then acidified with 120 ml concentrated hydrochloric acid, and extracted with diethyl ether (3×300 ml). The combined organic extracts were dried over magnesium sulfate, filtered and concentrated to yield 49.2 g of benzylmethylmalonic acid as a yellow solid (83% yield).

The benzylmethylmalonic acid (49.2 g) was dissolved in 400 ml of acetonitrile with 1.69 g of cuprous oxide and heated to reflux for 5 hours. The solvent was removed under vacuum. The residue was taken up in 400 ml of diethyl ether and rinsed with 10% hydrochloric acid (×300 ml), 300 ml of saturated sodium chloride, dried over magnesium sulfate, filtered and concentrated. The residue was purified by flash chromatography (5% to 10% methanol in chloroform) to yield 38.3 g of 2-benzylpropionic acid (99% yield).

The 2-benzylpropionic acid (38.3 g) was combined with 400 ml of 50% aqueous ethanol, 83.88 g quinine ·2H$_2$O and heated on a steam bath for 20 minutes to give a clear solution. After standing overnight, the crystals which formed were collected to yield 97.37 g of quinine salt. After six additional recrystallizations from 50% aqueous ethanol, there remained 18.8 g of the quinine salt.

The quinine salt (0.34 g) was treated with 100 ml of 1M sulfuric acid and extracted with chloroform (2×100 ml). The combined organic extracts were dried over magnesium sulfate, filtered and concentrated. The residue was purified by radial chromatography (5% to 10% methanol in chloroform, 2 mm plate) to yield 89 mg of (S)-2-methyl-3-phenylpropionic acid.

A 1.0 g quantity of (S)-2-methyl-3-phenylpropionic acid was combined with 0.67 ml of N-methylmorpholine, cooled to −20° C. and treated with 0.79 ml of isobutyl chloroformate. After 15 minutes, 1.38 g of 1,3-di-n-propyl-5,6-diaminouracil in 2 ml dimethylformamide was added. The reaction was allowed to warm to room temperature over 2 hours. The reaction was then poured into 300 ml of chloroform, rinsed with 200 ml of saturated sodium bicarbonate, 200 ml of saturated sodium chloride, dried over magnesium sulfate, filtered and concentrated. The residue was purified by radial chromatography (3% to 5% to 10% methanol in chloroform, 2 mm plate) and (10% to 15% isopropyl alcohol in hexane, 2 m plate) to yield 1.6 g of amide. This was purified by flash chromatography (3% to 5% to 10% methanol in chloroform) (5% to 10% isopropyl alcohol in hexane) to yield 1.05 g of amide. This was purified by radial chromatography (5% isopropyl alcohol in hexane, 2 mm plate) 5 to yield 0.44 g of amide.

The amide (430 mg) was dissolved in 40 ml of dry benzene and 7.5 ml of triethyloxonium tetrafluoroborate (1M in methylene chloride) was added. The reaction was heated to reflux for 5 hours. It was then poured into phosphate buffer, extracted with 300 ml toluene, dried over magnesium sulfate, filtered and concentrated. The residue was purified by radial chromatography (3% to 6% methanol in chloroform, 2 mm plate) to yield 209 mg of imino ether and 122 mg of starting material. The imino ether was again purified as above to yield 121 mg of pure chiral imino ether.

A 121 mg quantity of the chiral imino ether was dissolved in 14 ml of benzene and heated to reflux for 4 hours. Thin layer chromatography indicated complete reaction. The solvent was removed under vacuum and the residue purified by radial chromatography (50% ethyl acetate in hexane, 2 mm plate) to yield 87 mg of material which was recrystallized from 20% diethyl ether in hexane to yield 76 mg of 3,7-dihydro-8-[(S)-1-methyl-2-phenyl-ethyl]-1,3-dipropyl-1H-purine-2,6-dione after drying under vacuum at 60° C. for 2 hours as a white solid, m.p. 141°–142° C.

EXAMPLE 2

S-(+)-2-Phenylpropionic acid (0.69 g), 0.46 ml of N-methylmorpholine and 10 ml of tetrahydrofuran were combined and cooled to −20° C. An 0.46 ml volume of isobutyl chloro formate was added and the reaction was allowed to stir for 25 minutes. An 0.84 g quantity of 1,3-di-n-propyl-5,6-di-aminouracil in 5 ml of dimethylformamide was added and the reaction was stirred at −20° C. for 4 hours. The solution was then warmed to room temperature overnight. The solvent was removed under high vacuum and the residue was taken up in 300 ml of chloroform. The organic layer was rinsed with 200 ml of saturated sodium bicarbonate, 200 ml of saturated sodium chloride, dried over magnesium sulfate, filtered and concentrated. The residue was purified by flash chromatography (5% to 10% to 15% isopropyl alcohol in hexane) to yield 0.94 g of amide as a foam (69% yield).

The above amide (0.90 g) was dissolved in 50 ml of dry benzene, treated with 16.3 ml of triethyloxonium tetrafluoroborate (1M in methylene chloride) and heated to 50° C. for 15 hours. The solution was then poured into 300 ml of phosphate buffer and extracted with 400 ml of diethyl ether. The organic phase was rinsed with 300 ml of saturated sodium chloride, dried over magnesium sulfate, filtered and concentrated. The residue was purified by radial chromatography (3% to 5% to 10% methanol in chloroform, 2 mm plate) to yield 0.70 g of imino ether (72% yield).

The above imino ether (0.70 g) was dissolved in 50 ml of dry benzene and heated to reflux under nitrogen for 4 hours. The solvent was removed under high vacuum and the residue was purified by radial chromatography (50% ethyl acetate in hexane, 2 mm plate) to yield 0.415 g of product after recrystallization. This was dried under high vacuum over $P_2O_5$ to yield 0.413 g of product, m.p. 134.5–136° C. This was again recrystallized from 20% diethyl ether in hexane to yield 255 mg of product which was dried under high vacuum in a drying pistol at 39° C. for 20 hours to yield 252 mg of 3,7-dihydro-8-[(S)-1-phenylethyl]-1,3-dipropyl-1H-purine-2,,6-dione.

EXAMPLE 3

N-Valeric acid (1 g) was dissolved in 75 ml of tetrahydrofuran and treated with 2 equivalents of lithium diisopropylamide at room temperature. The solution was then heated to 40° C. for 30 minutes followed by the addition of 1.1 ml of benzyl chloride. After 1.5 hours at 40° C., the reaction mixture was cooled to room temperature, poured into 300 ml of water and extracted with diethyl ether (2×200 ml). The aqueous solution was then acidified with 1M hydrochloric acid and extracted with diethyl ether (2×300 ml). The combined organic extracts were dried over magnesium sulfate, filtered and concentrated. The residue was purified by radial chromatography (40–50% ethyl acetate in hexane, 2 mm plate) to yield 1.63 g of 2-benzylpentanoic acid (87% yield).

The 2-benzylpentanoic acid (0.88 g) was dissolved in 15 ml of tetrahydrofuran with 0.46 ml of N-methylmorpholine. The solution was cooled to −20° C. and 0.60 ml of isobutyl chloroformate was added. After 30 minutes, 0.84 g 1,3-di-n-propyl-5, 6-diaminouracil in 5 ml of dimethylformamide was added with stirring at −20° C. After 3 hours, the reaction was warmed to room temperature and the solvent was removed under high vacuum. The residue was purified by flash chromatography (5% to 10% isopropyl alcohol in hexane) to yield 0.55 g of the amide as a foam.

The amide (0.55 g) was combined with 20 ml of 30% potassium hydroxide and 5 ml of ethanol and heated to 80° C. with stirring for 5 hours. The solution was then cooled, acidified with concentrated hydrochloric acid, extracted with chloroform (3×200 ml), and the organic extracts were combined and dried over magnesium sulfate. The mixture was filtered and the filtrate was concentrated under vacuum. The residue was purified by radial chromatography (50% ethyl acetate in hexane, 2 mm plate). The product was triturated with 20% diethyl ether in hexane and dried under high vacuum, at 39° C., for 16 hours to yield 217 mg of 3,7-dihydro-8-[1-(phenylmethyl)butyl]-1,3-dipropyl-1H-purine-2,6-dione, m.p. 158°–160° C.

EXAMPLE 4

1,3-Diallyl-6-aminouracil (5 g) was suspended in 400 ml of water in a 1 L round bottom flask with overhead stirring. Acetic acid (6.7 ml of a 20% solution) was added, followed by intermittent addition of 2 ml of concentrated hydrochloric acid and a sodium nitrite solution (1.53 g in 7 ml water). After 4 hours, this solution was filtered, washed with water, collected and dried in a vacuum oven at 80° C. for 20 hours to yield 4.54 g of 1,3-diallyl-5-nitroso-6-aminouracil as a purple solid, m.p. 170°–180° C. (87% yield).

The 1,3-diallyl-5-nitroso-6-aminouracil (4.5 g) was suspended in 150 ml of ethyl acetate and treated with 23.6 g of sodium dithionite in 64 ml of water. After 1 hour, the layers were separated and the aqueous phase was extracted with ethyl acetate (4×100 ml). The combined organic extracts were dried over magnesium sulfate, filtered and concentrated and the residue was purified by flash chromatography (10% methanol in chloroform) to yield 4.41 g of 1,3-diallyl-5,6-diaminouracil.

Next, 2-phenylpropionic acid (1.0 g) was dissolved in 10 ml of acetonitrile with 0.73 ml of N-methylmorpholine at −20° C. Isobutyl chloroformate (0.86 ml) was added. After 15 minutes, 1.48 g of 1,3-diallyl-5,6-diaminouracil in 3 ml of dimethylformamide was added. After 4 hours, the reaction was warmed to room temperature and the solvent was removed under vacuum. The residue was purified twice by flash chromatography (3–5% methanol in chloroform) to yield 0.50 g of the amide.

The amide (0.50 g) was dissolved in 30 ml of dry benzene, treated with 9.2 ml of triethyloxonium tetrafluoroborate (1M in methylene chloride) and heated to 50° C. for 5 hours. After cooling, the reaction was poured into phosphate buffer (200 ml) and extracted with toluene (3×200 ml). The combined organic extracts were dried over magnesium sulfate, filtered and concentrated. The residue was dissolved in 100 ml of toluene and heated to 100° C. for 4 hours. After cooling, the solvent was removed under vacuum and the residue was purified by radial chromatography (50% ethyl acetate in hexane, 2 mm plate) to yield 0.45 g of a white solid, m.p. 142°–143° C. This solid was recrystallized from 30% diethyl ether in hexane to yield 280 mg of 3,7-dihydro-8-(1-phenylethyl)-1,3-di-2-propenyl-1H-purine-2,6-dione.

EXAMPLE 5

Diisopropylamine (3.2 ml) was dissolved in 20 ml of tetrahydrofuran, cooled to 0° C. and treated with 14.2 ml of 1.6M n-butyllithium. After 30 minutes, the lithium diisopropylamide was added to 1 g of n-butyric acid in 75 ml of tetrahydrofuran at −78° C. After 10 minutes the reaction was warmed to −20° C. After 10 more minutes the reaction was warmed slowly to room temperature. The solution was then heated to approximately 35° C. for 30 minutes and then cooled back to room temperature and 1.3 ml of benzyl chloride was added. After 1.5 hours the reaction mixture was heated to 35° C. for 2.5 hours. The solution was then cooled, diluted with 300 ml of water, rinsed with diethyl ether (2×200 ml), and the aqueous phase was acidified with 1M hydrochloric acid and extracted with diethyl ether (3×200 ml). The combined organic extracts were dried over magnesium sulfate, filtered and concentrated. The residue was purified by radial chromatography (50% ethyl acetate in hexane, 2 mm plate) to yield 1.56 g of 2-benzylbutyric acid (77% yield).

The 2-benzylbutyric acid (0.82 g) was dissolved in 10 ml of tetrahydrofuran, cooled to −20° C., and treated with 0.46 ml of N-methylmorpholine and 0.60 ml of isobutyl chloroformate. After 30 minutes, 0.84 g of 1,3-di-n-propyl-5,6-diaminouracil in 5 ml of dimethylformamide was added and the reaction mixture was allowed to stir at −20° C. for 4 hours. The solution was then allowed to warm to room temperature overnight. The solution was then diluted with 5 200 ml of methylene chloride and rinsed with saturated sodium bicarbonate (100 ml). The organic phase was dried over magnesium sulfate, filtered and concentrated under high vacuum. The residue was purified by flash chromatography (5% to 10% to 15% to 20% isopropyl alcohol in hexane) to yield 1.04 g of amide (71% yield).

The amide (1.04 g) was dissolved in 10 ml of ethanol, followed by the addition of 40 ml of 30% potassium hydroxide and heated to 90° C. for 1.5 hours. The solution was then allowed to cool to room temperature overnight, and acidified with concentrated hydrochloric acid. The reaction mixture was diluted with 200 ml water, extracted with chloroform (3×200 ml), and the combined organic extracts were dried over magnesium sulfate, filtered and concentrated. The residue was purified by radial chromatography (40–50% ethyl acetate in hexane, 2 mm plate) to yield 0.49 g of product. The product was triturated with 20% diethyl ether in hexane, and the white precipitate was collected and dried at 39° C. under high vacuum to yield 418 mg of 3,7-dihydro-8-[1-(phenylmethyl)propyl]-1,3-dipropyl-1H-purine-2,6-dione, m.p. 180° C.

The above product was again dried under high vacuum at 39° C. for 6 hours to yield 407 mg of 3,7-dihydro-8-[1-(phenylmethyl) propyl]-1,3-dipropyl-1H-purine-2,6-dione, m.p. 186°–187° C. This was dried over anhydrous phosphoric acid at 39° C. under high vacuum for 24 hours to yield 342 mg of final product 3,7-dihydro-8-[1-(phenylmethyl) propyl]-1,3-dipropyl-1H-purine-2,6-dione, m.p. 186°–188° C.

EXAMPLE 6

(R)-(−)-2-Phenylpropionic acid (0.69 g) was combined with 15 ml of tetrahydrofuran, 0.46 ml of N-methylmorpholine, and cooled to −20° C. and treated with 6.6 ml of isobutyl chloroformate. After 30 minutes, 0.84 g of 1,3-di-n-propyl-5,6-diaminouracil in 5 ml of dimethylformamide was added to the reaction, which was allowed to stir at −30° C. for 4 hours. The solution was then allowed to warm to room temperature over 15 hours and the solvent was removed under high vacuum. The residue was taken up in 300 ml of chloroform, and the organic phase was rinsed with 200 ml of saturated sodium bicarbonate, dried over magnesium sulfate, filtered and concentrated. The residue was purified by flash chromatography (5% to 10% to 15% to 20% isopropyl alcohol in hexane) to yield 1.21 g of the desired amide (89% yield).

The amide (1.1 g) was dissolved in 50 ml of benzene, treated with 19.9 ml of triethyloxonium tetrafluoroborate (1M in methylene chloride) and heated at 50° C. for 15 hours. The mixture was then cooled, poured into 300 ml of diethyl ether and rinsed with 200 ml of phosphate buffer, and 200 ml of water, 200 ml of saturated sodium chloride. The organic phase was dried over magnesium sulfate, filtered and concentrated. The residue was purified by radial chromatography (2% to 5% methanol in chloroform, 2 mm plate) to yield 0.65 g of desired imino ether.

The imino ether (0.65 g) was dissolved in 60 ml of dry benzene and heated at reflux for 4 hours. After cooling, the solvent was removed under vacuum and the residue was purified by radial chromatography (50% ethyl acetate in hexane, 2 mm plate) to yield 0.56 g of 3,7-dihydro-8-[(R)-1-phenylethyl]-1,3-dipropyl-1H-purine-2,6-dione, m.p. 136°–137° C.

EXAMPLE 7

2-Phenylpropionic acid (0.69 g) was dissolved in 15 ml of tetrahydrofuran, treated with 0.46 ml of N-methylmorpholine, cooled to −20° C. and 0.6 ml of isobutyl chloroformate was added. After 30 minutes, 0.84 g of 1,3-di-n-propyl-5, 6-diaminouracil in 5 ml of dimethylformamide was added. The reaction was allowed to stir at −20° C. for 4 hours and 5 then warmed to room temperature. The solvent was removed under high vacuum and the residue was purified by flash chromatography (5% to 10% to 15% to 20% isopropyl alcohol in hexane) to yield 0.96 g of desired amide (70% yield).

The amide (0.95 g) was combined with 10 ml of ethanol and 40 ml of 30% of aqueous potassium hydroxide and heated to 90° C. for 1.5 hours. The solution was then cooled in an ice bath and carefully acidified with concentrated hydrochloric acid. The reaction mixture was diluted with 100 ml of water and the aqueous layer was extracted with chloroform (3×200 ml). The combined organic extracts were dried over magnesium sulfate, filtered and concentrated to yield 0.91 g of product. The product was purified by radial chromatography (50% ethyl acetate in hexane, 2 mm plate) to yield 0.78 g of material which was recrystallized from 20% diethyl ether in hexane to yield 0.591 g of 3,7-dihydro-8-(1-phenylethyl)-1,3-dipropyl-1H-purine-2,6-dione, m.p. 148°–150° C.

EXAMPLE 8

Sodium hydride (15.2 g, 50% solution) was rinsed with 100 ml of tetrahydrofuran. It was then suspended in 300 ml of tetrahydrofuran, cooled to 0° C. and 50 g of diethyl methylmalonate dissolved in 75 ml of tetrahydrofuran was added dropwise over 45 minutes. After stirring an additional 30 minutes, 36.8 ml of benzyl chloride was added followed by 25 ml of tetrahydrofuran. The reaction mixture was then heated at gentle reflux for 3 hours, cooled, poured into 500 ml of water and extracted with ethyl acetate (3×500 ml). The combined organic extracts were dried over magnesium sulfate, filtered and concentrated to yield 75 g of diethyl benzylmethylmalonate.

The diethyl benzylmethylmalonate (75 g) was combined with 300 ml of ethanol and a solution of 100 g of potassium hydroxide in 300 ml of water and heated at gentle reflux for 5 hours. After cooling, the mixture was extracted with diethyl ether (2×300 ml). The aqueous layer was then acidified with 120 ml of concentrated hydrochloric acid and extracted with diethyl ether (3×300 ml). The combined organic extracts were dried over magnesium sulfate, filtered and concentrated to yield 49.2 g of benzylmethylmalonic acid as a yellow solid (83% yield).

The benzylmethylmalonic acid (49.2 g) was dissolved in 400 ml of acetonitrile, treated with 1.69 g of cuprous oxide and heated to reflux for 5 hours. The solvent was removed under vacuum and the residue taken up in 400 ml of diethyl ether and rinsed with 10% hydrochloric acid (2×300 ml), saturated sodium chloride (300 ml), dried over magnesium sulfate, filtered and concentrated. The residue was purified by flash chromatography (5% to 10% methanol in chloroform) to yield 38.37 g of 2-benzylpropionic acid (99% yield).

The 2-benzylpropionic acid (38.3 g) was combined with 400 ml of 50% aqueous ethanol, 83.88 g of quinine ·2H$_2$O and heated on a steam bath for 20 minutes to give a clear solution. After standing overnight, the crystals which formed were collected to yield 97.37 g of the quinine salt. After six additional recrystallizations from 50% aqueous ethanol there remained 18.8 g of the quinine salt.

The mother liquors from the above recrystallizations were acidified and extracted to yield 24.86 g of recovered 2-benzylpropionic acid. This acid was combined with 18.4 g of d-(+)-α-methylbenzylamine in 160 ml of ethyl acetate, dissolved by heating on a steam bath, cooled, and the precipitate was collected to yield 35 g of the amine salt. After three additional recrystallizations from ethyl acetate, the amine salt (0.4 g) was treated with 100 ml of 1M sulfuric acid. The aqueous layer was extracted with chloroform (2×100 ml) and the combined organic extracts dried over magnesium sulfate, filtered and concentrated. The residue was purified by radial chromatography (5% methanol in chloroform, 2 mm plate) to yield 186 mg of (R)-2-benzylpropionic acid.

(R)-2-Benzylpropionic acid (0.69 g) was dissolved in 15 ml of tetrahydrofuran and the solution was cooled to −20° C. and treated with 0.46 ml of N-methylmorpholine, 0.60 ml of isobutyl chloroformate and allowed to stir for 30 minutes. This was followed by the addition of 0.84 g of 1,3-di-n-propyl-5,6-diaminouracil in 5 ml of dimethylformamide and the reaction mixture was allowed to stir for an additional 4 hours at −20° C. The solution was allowed to warm to room temperature overnight. The solvent was removed under high vacuum and the purple residue was purified by flash chromatography (5% to 10% to 15% to 20% isopropyl alcohol in hexane) to yield 0.87 g of desired amide (64% yield).

The amide (0.85 g) was dissolved in 100 ml of dry benzene, treated with 14.8 ml of triethyloxonium tetrafluoroborate (1M in methylene chloride) and the solution was heated at 50° C. for 15 hours. The solution was then cooled, poured into 500 ml of diethyl ether and rinsed with 300 ml of phosphate buffer, 200 ml of saturated sodium chloride, dried over magnesium sulfate, filtered and concentrated. The residue was purified by radial chromatography (2% to 5% methanol in chloroform, 2 mm plate) to yield 0.36 g of desired imino ether.

The imino ether (0.36 g) was dissolved in 100 ml of dry benzene and heated to reflux for 3 hours. The solvent was removed under vacuum and the residue was purified by radial chromatography (50% ethyl acetate in hexane, 2 mm plate) to yield 0.23 g of 3,7-dihydro-8-[(R)-1-methyl-2-phenylethyl]-1,3-dipropyl-1H-purine-2,6-dione. This solid was recrystallized from 20% diethyl ether in hexane to yield, after drying under high vacuum at 39° C., 187 mg of 3,7-dihydro-8-[-(R)-1-methyl-2-phenylethyl]-1,3-dipropyl-1H-purine-2,6-dione, m.p. 141°–142° C.

EXAMPLE 9

β-Propiolactone (5.5 g) was dissolved in 100 ml of methanol and treated with 10.8 ml of triethylamine at room temperature with-stirring. After 3 days, the solvent was removed under vacuum and the residue was purified by flash chromatography (10% to 20% isopropyl alcohol in hexane) to yield 3.30 g of 3-hydroxymethyl propionate.

The 3-hydroxymethyl propionate (3.23 g) was dissolved in 100 ml tetrahydrofuran, cooled to −50° C. and treated with 2.1 eq. of lithium diisopropylamide in 100 ml tetrahydrofuran. After 20 minutes, 3.68 ml of benzyl bromide was added to the dianion at −50° C. The temperature was warmed to −20° C. over one hour. The reaction was then diluted with 500 ml of saturated ammonium chloride and the aqueous layer which formed was extracted with diethyl ether (2×500 ml). The combined organic extracts were dried over anhydrous magnesium sulfate, filtered, and concentrated. The crude residue was purified by flash chromatography (10% to 20% isopropyl alcohol in hexane) to yield 2.65 g of 2-benzyl-3-hydroxymethyl propionate.

The 2-benzyl-3-hydroxymethyl propionate (2.6 g) was dissolved in 75 ml of dry dimethylformamide under nitrogen. t-Butyldimethylsilyl chloride (2.2 g) was added with stirring, followed by the addition of 2.0 g of imidazole. After 1-½ hours the reaction was diluted with 500 ml of diethyl ether. The organic phase was rinsed with 50% aqueous sodium chloride (3×200 ml), saturated sodium chloride (300 ml), dried over anhydrous magnesium sulfate, filtered, and concentrated under vacuum. The residue was purified by flash chromatography (5% to 10% isopropyl alcohol in hexane) to yield 3.49 g of methyl 2-benzyl-3-(t-butyldimethylsilyloxy) propionate.

The methyl 2-benzyl-3-(t-butyldimethylsilyloxy) propionate (3.3 g) was dissolved in 100 ml of methanol, cooled to 0° C. and treated with 50 ml of 30% potassium hydroxide with vigorous stirring. The reaction was then allowed to warm to room temperature over five hours. The reaction was diluted with 200 ml of water, rinsed with diethyl ether, and the aqueous solution was cooled to 0° C. Dichloromethane (100 ml) was added, followed by the slow addition of 260 ml of 1M hydrochloric acid, with stirring. The layers were separated and the aqueous layer was extracted with dichloromethane (3×200 ml). The combined organic extracts were dried over anhydrous magnesium sulfate, filtered, and concentrated under vacuum. The residue was purified by radial chromatography (2% to 4% methyl alcohol in chloroform, 4 mm plate) to yield 2.14 g of the 2-benzyl-3-(t-butyldimethylsilyloxy)propionic acid.

The 2-benzyl-3-(t-butyldimethylsilyloxy)propionic acid (2.1 g) was dissolved in 20 ml of tetrahydrofuran, cooled to −20° C. and treated with 0.71 ml of N-methylmorpholine. Isobutyl chloroformate (0.92 ml) was then added and the reaction was allowed to stir for 20 minutes at −20° C. The 1,3-di-n-propyl-5,6-diaminouracil (1.62 g) in 10 ml of dimethylformamide was added and the reaction was stirred for 3 hours at −20° C. The reaction was then warmed to room temperature, diluted with 400 ml of chloroform and the organic phase rinsed with 50% aqueous sodium chloride (2×200 ml), saturated sodium bicarbonate (200 ml), dried over anhydrous magnesium sulfate, filtered, and concentrated under vacuum. The residue was purified by radial chromatography (5% to 10% methyl alcohol in chloroform, 4 mm plate) to yield 4.25 g of the amide.

The amide (3.1 g) was then dissolved in 50 ml of ethyl alcohol and treated with 100 ml of 30% potassium hydroxide. This was heated to reflux for 1.5 hours. After cooling to 0° C., the reaction was acidified with 42 ml of concentrated hydrochloric acid. The aqueous layer was extracted with chloroform (2×200 ml). The combined organic extracts were dried over anhydrous magnesium sulfate, filtered, and concentrated under vacuum. The residue was purified by radial chromatography (5% to 10% methyl alcohol in chloroform, 4 mm plate) and (5% to 10% to 20% isopropyl alcohol in hexane, 4 mm plate) to yield 1.1 g of crude material. This was triturated with 25% diethyl ether in hexane to yield 0.82 g of 3,7-dihydro-8-[1-(hydroxymethyl)-2-phenylethyl]-1,3-dipropyl-1H-purine-2,6-dione as a white solid, after drying under vacuum at 39° C. for 5 hours, m.p. 145°–146° C.

EXAMPLE 10

Sodium (3.7 g) was dissolved in 80 ml of ethyl alcohol, followed by the addition of 150 ml of diethyl ether. Diethyl malonate (12.5 ml) was added followed by 20 g of α,α-dibromo-o-xylene in 150 ml of diethyl ether with overhead stirring. The reaction was heated to reflux for 5 hours. The reaction was cooled, filtered, and the solvent was removed under vacuum. The residue was treated with a potassium hydroxide solution (20 g in 125 ml of water) and heated to reflux for 15 hours. The reaction was then cooled and rinsed with 200 ml of diethyl ether. The aqueous phase was acidified with 30% hydrochloric acid. The precipitate was collected and dried under vacuum over Drieruite for 5 hours to yield 8.86 g of indan-2,2-dicarboxylic acid.

The indan-2,2-dicarboxylic acid (8.86 g) was placed in a 500 ml, round-bottom flask and heated to 200° C. with stirring for 15 minutes. The reaction was then cooled to room temperature and recrystallized from 10% isopropyl alcohol in hexane to yield 1.77 g of indan-2-carboxylic acid. (See *J. Med. Chem.*, 23, 1995 (1989).)

The indan-2-carboxylic acid (1.0 g) was dissolved in 15 ml of tetrahydrofuran, treated with 0.62 ml of N-methylmorpholine, and cooled to −20° C. Isobutyl chloroformate (0.80 ml) was added and the reaction was stirred for 30 minutes at −20° C. The 1,3-di-n-propyl-5,6-diaminouracil (1.2 g) in 5 ml of dimethylformamide was then added and the reaction was stirred at −20° C. for 4 hours. After warming to room temperature, the reaction was poured into 300 ml of chloroform and rinsed with 50% aqueous sodium chloride (2×100 ml), saturated sodium bicarbonate (2×100 ml), dried over anhydrous magnesium sulfate, filtered, and concentrated under vacuum. The residue was purified by radial chromatography (5% to 10% methyl alcohol in chloroform, 4 mm plate) and (10% to 20% to 30% isopropyl alcohol in hexane, 4 mm plate) to yield 2.19 g of the amide.

The amide (2.19 g) was treated with 100 ml of 30% potassium hydroxide, 40 ml of ethyl alcohol and heated to reflux for 2 hours. The reaction was then cooled to 0° C. and acidified with 42 ml of concentrated hydrochloric acid. The precipitate was collected and dissolved in 300 ml of chloroform. The organic phase was rinsed with 200 ml of saturated sodium bicarbonate, dried over anhydrous magnesium sulfate, filtered, and concentrated under vacuum. The residue was triturated with 80% diethyl ether in hexane to yield, after drying under vacuum at 60° C., 1.10 g of 3,7-dihydro-8-(2-indanyl)-1,3-dipropyl-1H-purine-2,5-dione, m.p. 223°–224° C.

EXAMPLE 11

2-Phenylbutyric acid (1.1 g) was treated with 5,6-diamino-1,3-dipropyluracil to obtain the amide and was cyclized following the procedure in Example 7 to obtain 454 mg of 3,7-dihydro-8-[(±)-phenylpropyl]-1,3-dipropyl-1H-purine-2,6-dione, m.p. 137°–138° C.

EXAMPLE 12

(S)-(+)-2-Phenylbutyric acid (0.93 g) was treated with 5,6-diamino-1,3-dipropyluracil to obtain the amide, following the procedure in Example 6. The amide was converted to the imino ether, which was thermally cyclized following the procedure of Example 6 to obtain 547 mg of 3,7-dihydro-8-[(S)-phenylpropyl]-1,3-dipropyl-1H-purine-2,5-dione, m.p. 128°–131° C.

EXAMPLE 13

(R)-(−)-2-Phenylbutyric acid (0.98 g) was treated with 5,6-diamino-1,3-dipropyluracil to obtain the amide, following the procedure in Example 6. The amide was converted to the imino ether which was thermally cyclized following the procedure of Example 6 to obtain 190 mg of 3,7-dihydro-8-[(R)-phenylpropyl]-1,3-dipropyl-1H-purine-2,6-dione, m.p. 128°–130° C.

EXAMPLE 14

A 1.9 g quantity of 2-benzylpropanoic acid was treated with 0.65 g of potassium hydroxide in 60 ml of water, with stirring. To this solution was added 2.0 g of 5,6-diamino-1,3-dimethyluracil hydrate followed by 2.3 g of 1-ethyl-3-[3-

(dimethylamino)propyl]carbodiimide hydrochloride. After 2 hours, the solvent was removed and the residue purified by radial chromatography (40% isopropyl alcohol in hexane, 4 mm plate) to yield 1.85 g of material which was triturated with ether to yield 0.40 g of amide as a white solid.

The amide (0.33 g) was treated with 10 ml of 30% aqueous potassium hydroxide and 2 ml of ethyl alcohol and heated to 70° C. for 1.5 hours. After cooling, the reaction was acidified with 55 ml of 1M hydrochloric acid and extracted with 300 ml of ethyl ether. The organic phase was rinsed with 200 ml of water, 200 ml of saturated sodium chloride, dried over anhydrous magnesium sulfate, filtered, and concentrated. The residue was triturated with hexane to yield, after drying under vacuum over phosphorous pentaoxide, 142 mg of 3,7-dihydro-8-[(+)-(methyl-2-phenylethyl)]-1,3-dimethyl-1H-purine-2,6-dione, m.p. 198°–199° C.

EXAMPLE 15

A 22 g quantity of 4-benzyloxybenzyl chloride was treated with diethyl methylmalonate anion following the procedure in Example 8. The alkylated methylmalonate was saponified and decarboxylated following the same procedure to obtain 18.06 g of 2-(4-benzyloxybenzyl)propionic acid, m.p. 93°–95° C. A 3.6 g quantity of this acid was treated with 5,6-diamino-1,3-dipropyluracil to obtain the amide and was cyclized following the procedure in Example 7 to obtain 1.46 g of material which was recrystallized from 5% ethyl ether in hexane to yield 0.72 g of 3,7-dihydro-8-[methyl-2-(4-benzyloxyphenyl)ethyl]-1,3-dipropyl-1H-purine-2,6-dione, m.p. 124°–126° C. A 260 mg quantity of 3,7-dihydro-8-[methyl-2-(4-benzyloxyphenyl)ethyl]-1,3-dipropyl-1H-purine-2,6-dione was dissolved in 20 ml of methyl alcohol and treated with a catalytic amount of 5% palladium on charcoal. This was placed under an atmosphere of hydrogen for 2 hours with stirring. It was then filtered through Celite and the filtrate concentrated under vacuum. The residue was purified by radial chromatography (50% ethyl acetate in hexane, 4 mm plate) to yield 182 mg of material which was triturated with 5% ethyl ether in hexane to yield, after drying under high vacuum at 39° C. for 3 hours, 162 mg of 3,7-dihydro-8-[methyl-2-(4-hydroxyphenyl)ethyl]-1,3-dipropyl-1H-purine-2,6-dione, m.p. 218°–220° C.

What is claimed is:

1. The method of attenuating a cognitive deficit in a patient in need thereof comprising administering to the patient a compound according to the structure:

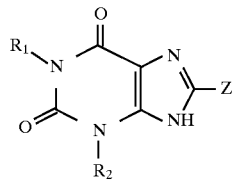

including the (R) and (S) enantiomers and racemic mixtures thereof, and the pharmaceutically acceptable salts thereof, wherein $R_1$ and $R_2$ are each independently ($C_1$–$C_4$) lower alkyl or ($C_2$–$C_4$) lower alkenyl, Z is:

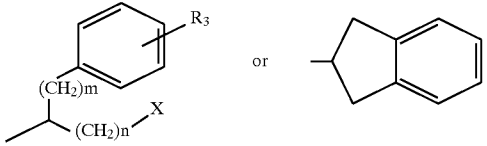

$R_3$ is ($C_1$–$C_3$) lower alkyl, nitro, amino, hydroxy, fluoro, bromo or chloro, m is zero or an integer from 1 to 4, n is an integer from 1 to 4, and X is H or OH.

2. The method of claim 1 wherein the compound is 3,7-dihydro-8-[(R)-1-methyl-2-phenylethyl]1,3-dipropyl-1H-purine-2,6-dione.

3. The method of claim 1 wherein the compound is (R)-1,3-dipropyl-8-(1-phenylpropyul)-xanthine.

4. The method of enhancing cognition in a patient in need thereof comprising administering to the patient a compound according to the structure:

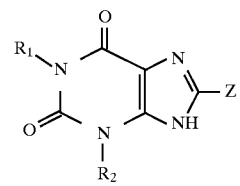

including the (R) and (S) enantiomers and racemic mixtures thereof, and the pharmaceutically acceptable salts thereof, wherein $R_1$ and $R_2$ are each independently ($C_1$–$C_4$) lower alkyl or ($C_2$–$C_4$) lower alkenyl, Z is:

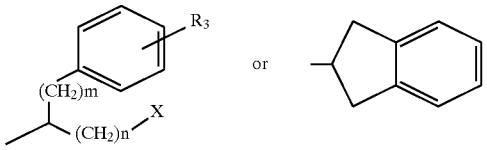

$R_3$ is ($C_1$–$C_3$) lower alkyl, nitro, amino, hydroxy, fluoro, bromo or chloro, m is zero or an integer from 1 to 4, n is an integer from 1 to 4, and X is H or OH.

5. The method of claim 4 wherein the compound is 3,7-dihydro-8-[(R)-1-methyl-2-phenylethyl]1,3-dipropyl-1H-purine-2,6-dione.

6. The method of claim 4 wherein the compound is (R)-1,3-dipropyl-8-(1-phenylpropyul)-xanthine.

* * * * *

UNITED STATES PATENT AND TRADEMARK OFFICE
CERTIFICATE OF CORRECTION

PATENT NO. : 5,840,729

DATED : Nov. 24, 1998

INVENTOR(S) : Janice M. Hitchock, et al

It is certified that error appears in the above-indentified patent and that said Letters Patent is hereby corrected as shown below:

Front page, in the Title, Line 2 reads "A1" and should read --$A_1$--.

Column 1, Line 2 reads "A1" and should read --$A_1$--.

Column 1 Line 4 reads "This present" and should read --The present--.

Column 4, Line 10 reads "" and should read --"†"--.

Column 5, Line 21 reads "A-2Adenosine" and should read --A-2 Adenosine--.

Column 5, Line 29 reads "50,000xg" and should read --50,000 x g--.

Column 5, Line 35 reads "[3H]" and should read --[$^3$H]--.

Column 7, Line 41 reads "(3.16)" and should read --(3,16)--.

Column 8, Line 16 reads "NaHCO3" and should read --$NaHCO_3$--.

Column 9, Line 30 reads "2phenylethyl" and should read --2-phenylethyl--.

Column 13, in Reaction Scheme IV, The Caption under are Structure in Line 2 reads "C" and should read --D--.

Column 17, Line 25 reads "formulations LO ranges" and should read --formulations ranges--.

Column 19, Line 23 reads "plate) 5 to" and should read --plate) to--.

Column 21, Lines 61 & 62 reads "with 5 200 ml" and should read --with 200 ml--.

UNITED STATES PATENT AND TRADEMARK OFFICE
CERTIFICATE OF CORRECTION

PATENT NO. : 5,840,729

DATED : Nov. 24, 1998

INVENTOR(S) : Janice M. Hitchock, et al

It is certified that error appears in the above-indentified patent and that said Letters Patent is hereby corrected as shown below:

Column 22, Lines 66 & 67 reads "and 5 then" and should read --and then--.

Signed and Sealed this

Seventeenth Day of April, 2001

Attest:

NICHOLAS P. GODICI

Attesting Officer     Acting Director of the United States Patent and Trademark Office